(12) United States Patent
Covert et al.

(10) Patent No.: US 12,106,125 B2
(45) Date of Patent: Oct. 1, 2024

(54) DEVELOPMENT ENVIRONMENT FOR GENERATION OF AUTOMATED CONTROL PATHWAYS

(71) Applicant: Evernorth Strategic Development, Inc., St. Louis, MO (US)

(72) Inventors: John Covert, Kennett Square, PA (US); David Spangler, Hilton Head, SC (US); Scott Betzel, Caledonia, IL (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 440 days.

(21) Appl. No.: 17/496,273

(22) Filed: Oct. 7, 2021

(65) Prior Publication Data
US 2023/0112311 A1    Apr. 13, 2023

(51) Int. Cl.
| | |
|---|---|
| G06F 9/451 | (2018.01) |
| G06F 3/0482 | (2013.01) |
| G06F 3/0484 | (2022.01) |
| G06F 8/34 | (2018.01) |
| G16H 20/10 | (2018.01) |
| G16H 40/20 | (2018.01) |
| G16H 70/40 | (2018.01) |
| G16H 70/60 | (2018.01) |

(52) U.S. Cl.
CPC ........... G06F 9/451 (2018.02); G06F 3/0482 (2013.01); G06F 3/0484 (2013.01); G06F 8/34 (2013.01); G16H 20/10 (2018.01); G16H 40/20 (2018.01); G16H 70/40 (2018.01); G16H 70/60 (2018.01)

(58) Field of Classification Search
CPC ...... G06F 9/451; G06F 3/0482; G06F 3/0484; G16H 70/60; G16H 40/20; G16H 70/40; G16H 20/10
See application file for complete search history.

(56) References Cited

U.S. PATENT DOCUMENTS

| | | |
|---|---|---|
| 8,032,397 B2 | 10/2011 | Lawless |
| 8,099,298 B2 | 1/2012 | Coleman |
| 8,543,421 B2 | 9/2013 | Menschik |
| 8,566,121 B2 | 10/2013 | Ramasubramanian |
| 8,898,576 B2 | 11/2014 | Schmidt |
| 9,218,608 B2 | 12/2015 | Smeeding |
| 10,334,056 B2 | 6/2019 | Olcese |

(Continued)

*Primary Examiner* — Matthew Ell
*Assistant Examiner* — Alvaro R Calderon, IV
(74) *Attorney, Agent, or Firm* — Harness IP

(57) ABSTRACT

A computerized method of generating an automated control pathway for a user interface includes displaying a graphical development environment having a palette area and multiple graphical programming elements, displaying a user selected question programming element and multiple associated pathway branches in the palette area, and assigning a received answer field to one of the branches. The method includes associating a selected determination programming element with one of the branches, and assigning a status value to the selected determination programming element that includes a drug request approval indication or a drug request denial indication. The method further includes running the automated control pathway to receive, via the user interface, an answer to a question associated with the selected question programming element, determining one of the branches associated with the received answer, and automatically transmitting an approval status or a denial status according to the determined branch.

16 Claims, 29 Drawing Sheets

(56) References Cited

U.S. PATENT DOCUMENTS

| | | |
|---|---|---|
| 10,475,140 B2 | 11/2019 | Patel |
| 10,552,928 B2 | 2/2020 | Schmidt-Lackner |
| 10,566,085 B2 | 2/2020 | Hanina |
| 10,719,839 B2 | 7/2020 | Smeeding |
| 10,769,242 B2 | 9/2020 | Aronow |
| 10,839,951 B2 | 11/2020 | Sysko |
| 10,868,751 B2 | 12/2020 | Shammari |
| 10,977,702 B2 | 4/2021 | Patel |
| 2004/0024634 A1 | 2/2004 | Carp |
| 2009/0320088 A1 | 12/2009 | Gill |
| 2014/0040136 A1 | 2/2014 | Shueler |
| 2015/0254428 A1 | 9/2015 | Burkett |
| 2015/0324547 A1 | 11/2015 | Graham |
| 2016/0104260 A1 | 4/2016 | Menrad |
| 2016/0117471 A1 | 4/2016 | Belt |
| 2016/0125550 A1 | 5/2016 | Joao |
| 2016/0148097 A1 | 5/2016 | Genova, III |
| 2016/0283676 A1 | 9/2016 | Lyon |
| 2016/0292378 A1 | 10/2016 | Saric |
| 2016/0357919 A1 | 12/2016 | Bojorquez |
| 2016/0358279 A1 | 12/2016 | Ghouri |
| 2017/0076058 A1 | 3/2017 | Stong |
| 2017/0091416 A1 | 3/2017 | Mink |
| 2017/0208022 A1 | 7/2017 | Drazin |
| 2020/0345299 A1 | 11/2020 | Goldsmith |
| 2021/0074401 A1 | 3/2021 | Bezdek |
| 2021/0210185 A1 | 7/2021 | Allred |

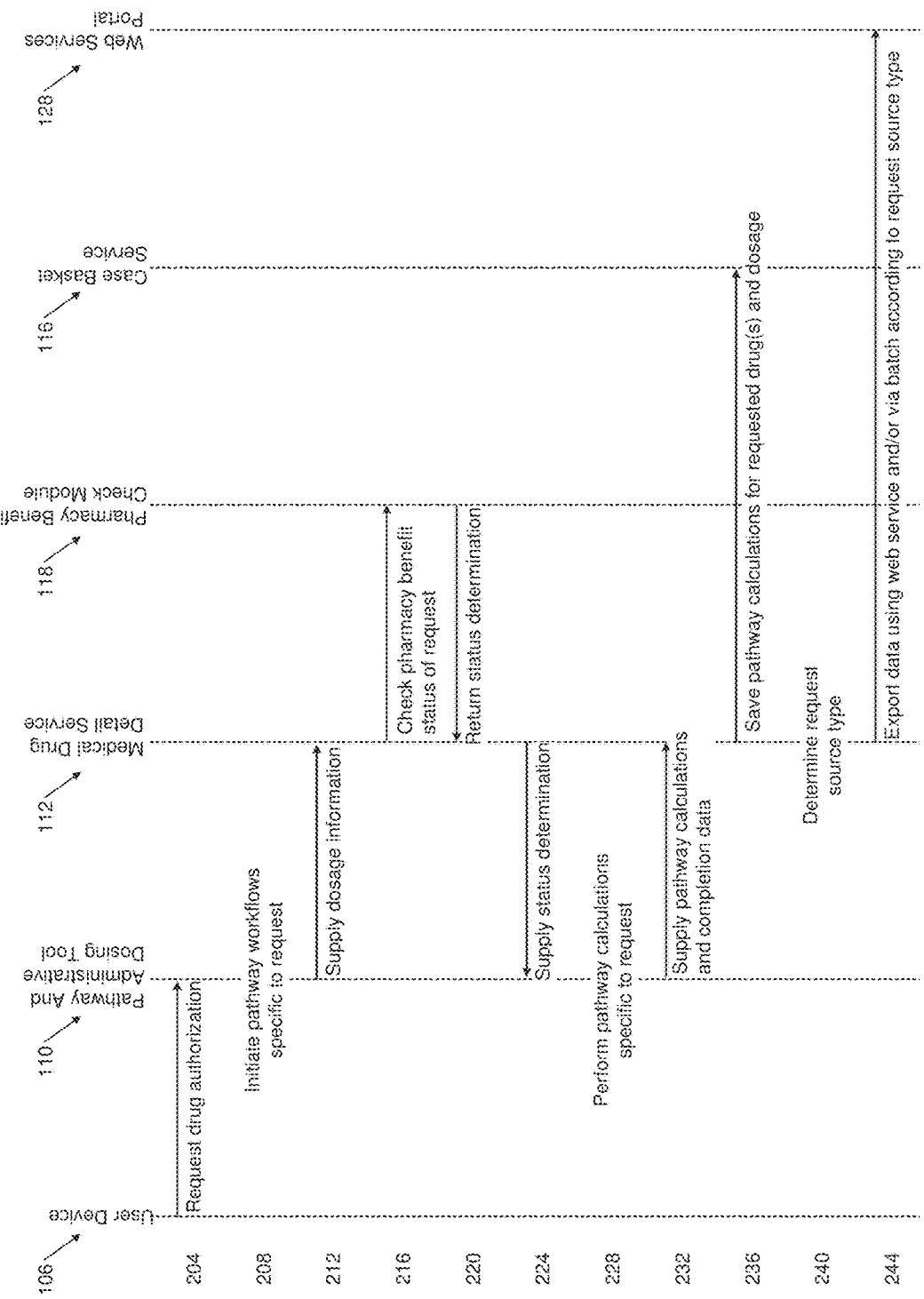

① Select Treatment Option:

| Regimen | Preferred Regimen | Risk of Neutropenia | Risk of Emesis | Total Cost of Care During Therapy | Selection Frequency |
|---|---|---|---|---|---|
| ○ Capecitabine + Gemcitabine | # | #### | #### | $####,#### | ##% |
| ○ Doxorubicin HCL + Gemcitabine | # | #### | #### | $####,#### | ##% |
| ⦿ Temsirolimus | # | #### | #### | $####,#### | ##% |
| ○ Build a Custom Treatment Plan (May Require Additional Clinical Review) | | | | | |

Submit

FIG. 20

Regimen | Regimen Group | Procedure-Organization | Organization | Procedure

Procedure Search
Procedure Code [J9035]   Description [          ]   Medical Discipline [          ]
[Search] [Reset]
Add New Procedure

| | Procedure Code | Description | Alt Description | Medical Discipline | Multiplier | Unit Cost | Unit Type | Medical Category | Is Ready For Promotion | Last Promoted On |
|---|---|---|---|---|---|---|---|---|---|---|
| Edit | J9035 | Bevacizmab | Avastin | Medical Oncology | 1 | 75.05 | Milligrams Per Kilograms | Situational | ☐ | |

Edit Procedure

Procedure Code
[J9035]

Procedure Code Set
[CPTHCPCS ˅]

Procedure Name
[J9035]

Description
[Bevacizmab]

Alternate Descriptions
[Avastin] ⊖
⊕

Descipline
[Medical Oncology]

Unit Type
[Mg/kg ˅]

Ready For Promotion
☐

Max HCPCS Units - RJ Health
[201]

Max HCPCS Units - MUE
[170]

Max HCPCS Units - Other
[170]

HCPCValue
[10.00]

Medicare Category
[Situational ˅]

Unit Cost
[75.05]

Multiplier
[1 ˅]

Health Plan
| CIGNA |

Ready For Promotion
☐

Drug Administration Technique
| Injectable ⌄ |

Display in BYOI List
☑

Display in Approved Drugs List
☑

Display in CarriersWeb
☐

Display in ImageOne
☐

Drug Class
| Chemo ⌄ |

Medicaid
☑

Medicare
☐

Commercial
☐

FIG. 22B

Treatment Procedures | Treatment Qualifiers

Add New

| | Treatment id | Description | Quantity | Expiration Period | Admin Notes | Amount | Unit | Multiplier | Doses per Cycle | Cycles Per Treatment | |
|---|---|---|---|---|---|---|---|---|---|---|---|
| Save Cancel | | J9035 - Bevacizmab ∨ | 1 | 0 | IV over | 15 | Mg/kg | 1 | 1 | 6 | 450.299999 99999995 |
| Edit Delete | 484 | J9045 - Carboplatin | 1 | 0 | IV over 30 minutes Day 1 every 21 days (following Bevacizumab + Paclitaxel) | 6 | AUC | 1 | 1 | 6 | 15.78 |
| Edit Delete | 485 | J9267 - Paclitaxel | 1 | 0 | IV over 3 hours Day 1 every 21 days | 200 | Mg/m2 | 1 | 1 | 6 | 0.72 |
| Edit Delete | 15564 | Q5107 - Bevacizmab-Awwb | 1 | 0 | IV over 90 minutes Day 1 every 21 days | 15 | Mg/kg | 1 | 1 | 6 | 354.659999 99999997 |
| Edit Delete | 15565 | Q5118 - Bevacizmab-bvzr | 1 | 0 | IV over 90 minutes Day 1 every 21 days | 15 | Mg/kg | 1 | 1 | 6 | 357.6 |

FIG. 23

DEVELOPMENT ENVIRONMENT FOR GENERATION OF AUTOMATED CONTROL PATHWAYS

FIELD

The present disclosure relates to development environments for generation of automated control pathways.

BACKGROUND

The field of medical oncology is experiencing continuing increases to treatment management complexity for various reasons, including increased use of specialty medications, a newer generation of treatments that target specific genetic pathways, an increased number of people living with cancer, unwarranted variations in treatment practices resulting in utilization of ineffective treatments, and avoidable ER visits and hospitalizations due to drug toxicities and poor pain management. Approximately 1% or more of some health plan customers may be in active treatment for cancer at any given time, which may contribute to up to 13% or more of a total medical cost (TMC) for a health plan provider. In some cases, cancer drugs may account for up to 25% or more of total spending in oncology care, with drug costs continuing to rise every year.

Medical oncology treatments may include multiple drugs that can be combined into different drug regimens, and evidence based guidelines are sometimes used by providers to select specific drugs for treating patients. Prescription drugs may be covered for patients under pharmacy benefits or medical benefits, and may each require a drug authorization before a health plan provider will pay an insurance benefit for a drug.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method of generating an automated control pathway for a user interface includes displaying a graphical development environment for generation of an automated control pathway for a prescription drug authorization request. The graphical development environment includes a palette area and multiple graphical programming elements. The multiple graphical programming elements include at least a question programming element and a determination programming element. The instructions include receiving a selection of the question programming element, displaying the selected question programming element at a location in the palette area specified via user input, receiving, via user input, at least one answer field specified for the selected question programming element, and displaying at least two pathway branches in the palette area. The at least two pathway branches are associated with the selected question programming element, and the at least one answer field is assigned to one of the at least two pathway branches according to user input. The instructions include receiving a selection of the determination programming element, associating, via user input, the selected determination programming element with one of the at least two pathway branches, and assigning a status value to the selected determination programming element according to user input. The status value includes a drug request approval indication or a drug request denial indication. The instructions include saving the automated control pathway in a production database. The automated control pathway includes the selected question programming element, the selected determination programming element, and the assigned status value for the selected determination programming element. The instructions include running the automated control pathway to display a question associated with the selected question programming element on a user interface, receiving, via the user interface, an answer to the displayed question, determining one of the at least two pathway branches associated with the received answer, and automatically transmitting an approval status or a denial status according to the status value assigned to the selected determination programming element associated with the determined one of the at least two pathway branches.

In other features, the method includes, prior to saving the automated control pathway in a production database, receiving a pathway validation request, and in response to a determination that the automated control pathway does not include any one of multiple specified major error warnings, saving the automated control pathway to a testing environment. Each specified major error warning defines an error in logic of the automated control pathway that prevents operation of the automated control pathway on a user interface.

In other features, the method includes, in response to a determination that the automated control pathway includes at least one specified major error warning, displaying the at least one specified major error warning, preventing saving of the automated control pathway to the testing environment at least until a pathway revision is received, and receiving at least one pathway revision via the graphical development environment. In other features, the method includes, in response to a determination that the automated control pathway includes at least one of multiple specified minor error warnings, displaying the at least one of the specified minor error warnings, where each specified minor error warning defines an issue in logic of the automated control pathway that does not prevent operation of the automated control pathway on the user interface.

In other features, the method includes performing at least one testing operation on the automated control pathway in the testing environment, and in response to an integration environment request received via user input, deploying the automated control pathway to an integration environment. In other features, the method includes receiving a selection of a plug-in programming element, displaying the selected plug-in programming element at a location in the palette area specified via user input, and assigning a call address to the selected plug-in programming element according to user input. The call address specifies an address of a component outside the automated control pathway for the plug-in programming element to retrieve data from.

In other features, the method includes receiving a selection of a link programming element, displaying the selected link programming element at a location in the palette area specified via user input, and assigning a pathway link to the selected link programming element according to user input. The pathway link specifies a pathway connection between the automated control pathway and another pathway outside of the automated control pathway.

In other features, the method includes receiving, via user input, at least one other field specified for the selected question programming element, where the at least one other field includes at least one of a question type field that specifies a type of answer supplied to the question programming element, an answer groups field that lists answer choices a user selects from during operation of the automated control pathway, and a validators field that sets rules for an answer submitted by a user for the question programming element. In other features, the method includes receiving, via the user interface, at least one clinical response indicative of a patient condition, identifying, via the automated control pathway, at least one drug regimen associated with treatment of the patient condition, and displaying the identified at least one drug regimen via the user interface for selection by a user.

In other features, the method includes receiving a selection of the at least one drug regimen via the user interface, and in response to a determination that the selected drug regimen is a national comprehensive cancer network (NCCN) recommended drug regimen, automatically transmitting an approval of an authorization request for the selected drug regimen.

A computer system includes memory hardware configured to store computer-executable instructions, and processor hardware configured to execute the instructions. The instructions include displaying a graphical development environment for generation of an automated control pathway for a prescription drug authorization request. The graphical development environment includes a palette area and multiple graphical programming elements. The multiple graphical programming elements include at least a question programming element and a determination programming element. The instructions include receiving a selection of the question programming element, displaying the selected question programming element at a location in the palette area specified via user input, receiving, via user input, at least one answer field specified for the selected question programming element, and displaying at least two pathway branches in the palette area. The at least two pathway branches are associated with the selected question programming element, and the at least one answer field is assigned to one of the at least two pathway branches according to user input. The instructions include receiving a selection of the determination programming element, associating, via user input, the selected determination programming element with one of the at least two pathway branches, and assigning a status value to the selected determination programming element according to user input. The status value includes a drug request approval indication or a drug request denial indication. The instructions include saving the automated control pathway in a production database. The automated control pathway includes the selected question programming element, the selected determination programming element, and the assigned status value for the selected determination programming element. The instructions include running the automated control pathway to display a question associated with the selected question programming element on a user interface, receiving, via the user interface, an answer to the displayed question, determining one of the at least two pathway branches associated with the received answer, and automatically transmitting an approval status or a denial status according to the status value assigned to the selected determination programming element associated with the determined one of the at least two pathway branches.

In other features, the computer system includes, prior to saving the automated control pathway in a production database, receiving a pathway validation request, and in response to a determination that the automated control pathway does not include any one of multiple specified major error warnings, saving the automated control pathway to a testing environment. Each specified major error warning defines an error in logic of the automated control pathway that prevents operation of the automated control pathway on a user interface.

In other features, the instructions further include, in response to a determination that the automated control pathway includes at least one specified major error warning, displaying the at least one specified major error warning, preventing saving of the automated control pathway to the testing environment at least until a pathway revision is received, and receiving at least one pathway revision via the graphical development environment. In other features, the instructions further include, in response to a determination that the automated control pathway includes at least one of multiple specified minor error warnings, displaying the at least one of the specified minor error warnings, where each specified minor error warning defines an issue in logic of the automated control pathway that does not prevent operation of the automated control pathway on the user interface.

In other features, the instructions further include performing at least one testing operation on the automated control pathway in the testing environment, and in response to an integration environment request received via user input, deploying the automated control pathway to an integration environment. In other features, the instructions further include receiving a selection of a plug-in programming element, displaying the selected plug-in programming element at a location in the palette area specified via user input, and assigning a call address to the selected plug-in programming element according to user input. The call address specifies an address of a component outside the automated control pathway for the plug-in programming element to retrieve data from.

In other features, the instructions further include receiving a selection of a link programming element, displaying the selected link programming element at a location in the palette area specified via user input, and assigning a pathway link to the selected link programming element according to user input. The pathway link specifies a pathway connection between the automated control pathway and another pathway outside of the automated control pathway.

In other features, the instructions further include receiving, via user input, at least one other field specified for the selected question programming element. The at least one other field includes at least one of a question type field that specifies a type of answer supplied to the question programming element, an answer groups field that lists answer choices a user selects from during operation of the automated control pathway, and a validators field that sets rules for an answer submitted by a user for the question programming element.

In other features, the instructions further include receiving, via the user interface, at least one clinical response indicative of a patient condition, identifying, via the automated control pathway, at least one drug regimen associated with treatment of the patient condition, and displaying the identified at least one drug regimen via the user interface for selection by a user. In other features, the instructions further include receiving a selection of the at least one drug regimen via the user interface, and in response to a determination that the selected drug regimen is a national comprehensive cancer network (NCCN) recommended drug regimen, automatically transmitting an approval of an authorization request for the selected drug regimen.

A computerized method of real-time automated request programming using application programming interfaces (APIs) includes receiving structured patient data at a pharmacy system infrastructure. The structured patient data is indicative of a patient database entry. The method includes executing an eligibility API call to an eligibility service module to obtain structured member eligibility data indicative of a prescription drug coverage status associated with the patient database entry, and obtaining, by the pharmacy system infrastructure, an authorization request including structured drug regimen data. The structured drug regimen data includes multiple drug database entries. The method includes executing a drug benefit API call to a claims engine to obtain structured drug benefit data associated with each of the multiple drug database entries of the structured drug regimen data, and for each of the multiple drug database entries, generating a drug authorization request according to the structured drug benefit data associated with the drug database entry and executing a drug authorization API call to an authorization engine, using the generated drug authorization request, to obtain an authorization approval or an authorization denial corresponding to the drug database entry. In response to receiving an authorization approval for each of the multiple drug database entries, the method includes transmitting a drug regimen approval status indicative of successful authorization for all of the multiple drug database entries in the structured drug regimen data. In response to receiving an authorization denial for at least one of the multiple drug database entries, the method includes transmitting a drug regimen denial status indicative of unsuccessful authorization of at least one of the multiple drug database entries in the structured drug regimen data.

In other features, executing an eligibility API call includes executing the eligibility API call via a member eligibility web service between the pharmacy system infrastructure and eligibility data module, executing a drug benefit API call includes executing a drug benefit API call via a drug benefit web service between the pharmacy system infrastructure and the claims engine, and executing the drug authorization API call includes executing the drug authorization API call via an authorization web service between the pharmacy system infrastructure and the authorization engine. In other features, each of the member eligibility web service, the drug benefit web service, and the authorization web service are configured to transfer a machine-readable file having at least one of an extensible markup language (XML) format and a JavaScript Object Notation (JSON) format.

In other features, each of the member eligibility web service, the drug benefit web service and the authorization web service are configured to implement a representational state transfer (REST) for execute each API call as a RESTful API, and executing the eligibility API call to the eligibility service module includes obtaining the structured member eligibility data in less than one second. In other features, the pharmacy system infrastructure includes a pharmacy API cache database configured to store at least one of the structured patient data, the structured member eligibility data, the structured drug regimen data, and the structured drug benefit data. The method includes transferring data from the pharmacy API cache database to a pharmacy data store via an outbound extract, transfer and load (ETL) scheduled service.

In other features, the method includes executing a claims service API call to a pharmacy claim database to store a log of structured compliance data associated with each authorization approval and with each authorization denial. In other features, the method includes, in response to the structured drug benefit data indicating that one of the multiple drug database entries is not covered for the patient database entry, identifying another drug database entry to replace the one of the multiple drug database entries that is not covered for the patient database entry. The identified another drug database entry and the replaced one of the multiple drug database entries are related to one another via at least one national drug code (NDC).

In other features, the method includes, in response to the structured member eligibility data indicating that the patient database entry does not have prescription drug coverage, transmitting an ineligible member denial notification and denying the authorization request. In response to the structured member eligibility data indicating that a health plan associated with the patient database entry does not include prescription drug coverage, the method includes transmitting an ineligible health plan denial notification and denying the authorization request.

In other features, the method includes identifying whether each of the multiple drug database entries are covered under medical benefits or pharmacy benefits, according to the structured drug benefit data, exporting each drug identified as covered under pharmacy benefits to a claim processor, and saving each drug identified as covered under medical benefits for claim processing via a scheduled periodic batch process. In other features, each API call is executed sequentially via an automated control pathway implemented by the pharmacy system infrastructure without user intervention.

A computer system includes memory hardware configured to store computer-executable instructions, and processor hardware configured to execute the instructions. The instructions include receiving structured patient data at a pharmacy system infrastructure. The structured patient data is indicative of a patient database entry. The instructions include executing an eligibility API call to an eligibility service module to obtain structured member eligibility data indicative of a prescription drug coverage status associated with the patient database entry, and obtaining, by the pharmacy system infrastructure, an authorization request including structured drug regimen data. The structured drug regimen data includes multiple drug database entries. The instructions include executing a drug benefit API call to a claims engine to obtain structured drug benefit data associated with each of the multiple drug database entries of the structured drug regimen data, and for each of the multiple drug database entries, generating a drug authorization request according to the structured drug benefit data associated with the drug database entry and executing a drug authorization API call to an authorization engine, using the generated drug authorization request, to obtain an authorization approval or an authorization denial corresponding to the drug database entry. In response to receiving an authorization approval for each of the multiple drug database entries, the instructions include transmitting a drug regimen approval status indicative of successful authorization for all of the multiple drug database entries in the structured drug regimen data. In response to receiving an authorization denial for at least one of the multiple drug database entries, the instructions include transmitting a drug regimen denial status indicative of unsuccessful authorization of at least one of the multiple drug database entries in the structured drug regimen data.

In other features, executing an eligibility API call includes executing the eligibility API call via a member eligibility web service between the pharmacy system infrastructure and eligibility data module, executing a drug benefit API call includes executing a drug benefit API call via a drug benefit web service between the pharmacy system infrastructure and the claims engine, and executing the drug authorization API call includes executing the drug authorization API call via an authorization web service between the pharmacy system infrastructure and the authorization engine. In other features, each of the member eligibility web service, the drug benefit web service, and the authorization web service are configured to transfer a machine-readable file having at least one of an extensible markup language (XML) format and a JavaScript Object Notation (JSON) format.

In other features, each of the member eligibility web service, the drug benefit web service and the authorization web service are configured to implement a representational state transfer (REST) for execute each API call as a RESTful API, and executing the eligibility API call to the eligibility service module includes obtaining the structured member eligibility data in less than one second. In other features, the pharmacy system infrastructure includes a pharmacy API cache database configured to store at least one of the structured patient data, the structured member eligibility data, the structured drug regimen data, and the structured drug benefit data. The instructions include transferring data from the pharmacy API cache database to a pharmacy data store via an outbound extract, transfer and load (ETL) scheduled service.

In other features, the instructions further include executing a claims service API call to a pharmacy claim database to store a log of structured compliance data associated with each authorization approval and with each authorization denial. In other features, the instructions further include, in response to the structured drug benefit data indicating that one of the multiple drug database entries is not covered for the patient database entry, and identifying another drug database entry to replace the one of the multiple drug database entries that is not covered for the patient database entry. The identified another drug database entry and the replaced one of the multiple drug database entries are related to one another via at least one national drug code (NDC).

In other features, the instructions further include, in response to the structured member eligibility data indicating that the patient database entry does not have prescription drug coverage, transmitting an ineligible member denial notification and denying the authorization request. In response to the structured member eligibility data indicating that a health plan associated with the patient database entry does not include prescription drug coverage, the instructions include transmitting an ineligible health plan denial notification and denying the authorization request.

In other features, the instructions further include identifying whether each of the multiple drug database entries are covered under medical benefits or pharmacy benefits, according to the structured drug benefit data, exporting each drug identified as covered under pharmacy benefits to a claim processor, and saving each drug identified as covered under medical benefits for claim processing via a scheduled periodic batch process. In other features, each API call is executed sequentially via an automated control pathway implemented by the pharmacy system infrastructure without user intervention.

A computerized method of automated linking management of regimen database entries includes receiving one or more clinical responses via a user interface. The one or more clinical responses are indicative of at least one medical condition of a patient. The method includes searching a production database to identify a regimen group database entry according to the received one or more clinical responses. The regimen group database entry is linked with multiple drug regimen database entries associated with the at least one medical condition of the patient. Each of the multiple drug regimen database entries is linked with multiple drug database entries. The method includes obtaining each drug regimen database entry linked with the identified regimen group database entry in the production database, displaying each of the obtained drug regimen database entries linked with the identified regimen group database entry on the user interface, receiving a selection of one of the displayed drug regimen database entries via the user interface, and obtaining, from the production database, structured drug attribute data for each drug database entry linked with the selected drug regimen database entry. The structured drug attribute data for each drug regimen database entry includes structured dosage data for the drug database entry. In response to receiving a regimen authorization request via the user interface, the method includes generating a drug authorization request for each drug database entry linked with the selected drug regimen database entry, with each drug authorization request including at least a portion of the structured drug attribute data for the drug database entry, and transmitting the generated drug authorization requests to a claim processing engine.

In other features, the method includes receiving structured organization data via the user interface. The structured organization data is indicative of an insurance provider organization associated with the patient. For each drug database entry linked with the selected drug regimen database entry, the method includes determining whether an organization modifier value is linked with the drug database entry in the production database according to the structured organization data, and in response to a determination that an organization modifier value is linked with the drug database entry, modifying the structured drug attribute data for the drug database entry prior to generating the drug authorization request for the drug database entry.

In other features, the method includes, for each drug database entry linked with the selected drug regimen database entry, determining whether an interchange value is linked with the drug database entry in the production database, where the interchange value specifies a replacement drug for substitution in treatment of the at least one medical condition of the patient, and in response to a determination that an interchange value is linked with the drug database entry, substituting the replacement drug for the drug database entry and generating a drug authorization request for the substituted replacement drug. In other features, the method includes receiving, via a database administrator user interface, a modification input for at least one of the regimen group database entry, the multiple drug regimen database entries, the multiple drug regimen database entries, and the structured drug attribute data. The method includes modifying, in a staging database, the at least one of the regimen group database entry, the multiple drug regimen database entries, the multiple drug regimen database entries, and the structured drug attribute data, according to the modification input.

In other features, the method includes receiving a promotion request input via the database administrator user interface, and promoting, to the production database, a copy of the modified at least one of the regimen group database entry, the multiple drug regimen database entries, the multiple drug regimen database entries, and the structured drug attribute data. In other features, the method includes receiving updated drug attribute data for at least one of the multiple drug database entries from an external vendor, and modifying, in the staging database, the at least one of the multiple drug database entries according to the updated drug attribute data.

In other features, the production database is configured to store multiple regimen group database entries, at least one of the drug database entries is linked with multiple drug regimen database entries in the production database, and at least one of the multiple drug regimen database entries is linked with multiple regimen group database entries in the production database. In other features, the production database is configured to store multiple treatment group database entries, each treatment group database entry includes multiple drug database entries, and each treatment group database entry is linked with multiple drug regimen database entries in the production database.

In other features, searching the production database to identify the regimen group database entry includes executing an automated control pathway including multiple branches. Each of the multiple branches is associated with a different regimen group database entry. The automated control pathway is configured to select different ones of the multiple branches according to different clinical responses received via the user interface. In other features, the method includes displaying a custom regimen build option on the user interface in addition to the obtained drug regimen database entries, and in response to receiving a selection of the custom regimen build option, displaying multiple drug database entries for selection by a user via the user interface.

A computer system includes memory hardware configured to store computer-executable instructions, and processor hardware configured to execute the instructions. The instructions include receiving one or more clinical responses via a user interface. The one or more clinical responses are indicative of at least one medical condition of a patient. The instructions include searching a production database to identify a regimen group database entry according to the received one or more clinical responses. The regimen group database entry is linked with multiple drug regimen database entries associated with the at least one medical condition of the patient. Each of the multiple drug regimen database entries is linked with multiple drug database entries. The instructions include obtaining each drug regimen database entry linked with the identified regimen group database entry in the production database, displaying each of the obtained drug regimen database entries linked with the identified regimen group database entry on the user interface, receiving a selection of one of the displayed drug regimen database entries via the user interface, and obtaining, from the production database, structured drug attribute data for each drug database entry linked with the selected drug regimen database entry. The structured drug attribute data for each drug regimen database entry includes structured dosage data for the drug database entry. In response to receiving a regimen authorization request via the user interface, the instructions include generating a drug authorization request for each drug database entry linked with the selected drug regimen database entry, where each drug authorization request includes at least a portion of the structured drug attribute data for the drug database entry, and transmitting the generated drug authorization requests to a claim processing engine.

In other features, the instructions include receiving structured organization data via the user interface. The structured organization data is indicative of an insurance provider organization associated with the patient. For each drug database entry linked with the selected drug regimen database entry, the instructions include determining whether an organization modifier value is linked with the drug database entry in the production database according to the structured organization data, and in response to a determination that an organization modifier value is linked with the drug database entry, modifying the structured drug attribute data for the drug database entry prior to generating the drug authorization request for the drug database entry.

In other features, the instructions include, for each drug database entry linked with the selected drug regimen database entry, the instructions include determining whether an interchange value is linked with the drug database entry in the production database, where the interchange value specifies a replacement drug for substitution in treatment of the at least one medical condition of the patient, and in response to a determination that an interchange value is linked with the drug database entry, substituting the replacement drug for the drug database entry and generating a drug authorization request for the substituted replacement drug. In other features, the instructions include receiving, via a database administrator user interface, a modification input for at least one of the regimen group database entry, the multiple drug regimen database entries, the multiple drug regimen database entries, and the structured drug attribute data, and modifying, in a staging database, the at least one of the regimen group database entry, the multiple drug regimen database entries, the multiple drug regimen database entries, and the structured drug attribute data, according to the modification input.

In other features, the instructions include receiving a promotion request input via the database administrator user interface, and promoting, to the production database, a copy of the modified at least one of the regimen group database entry, the multiple drug regimen database entries, the multiple drug regimen database entries, and the structured drug attribute data. In other features, the instructions include receiving updated drug attribute data for at least one of the multiple drug database entries from an external vendor, and modifying, in the staging database, the at least one of the multiple drug database entries according to the updated drug attribute data.

In other features, the production database is configured to store multiple regimen group database entries, at least one of the drug database entries is linked with multiple drug regimen database entries in the production database, and at least one of the multiple drug regimen database entries is linked with multiple regimen group database entries in the production database. In other features, the production database is configured to store multiple treatment group database entries, each treatment group database entry includes multiple drug database entries, and each treatment group database entry is linked with multiple drug regimen database entries in the production database.

In other features, searching the production database to identify the regimen group database entry includes executing an automated control pathway including multiple branches. Each of the multiple branches is associated with a different regimen group database entry. The automated control pathway is configured to select different ones of the multiple branches according to different clinical responses received via the user interface. In other features, the instructions include displaying a custom regimen build option on the user interface in addition to the obtained drug regimen database entries, and in response to receiving a selection of the custom regimen build option, displaying multiple drug database entries for selection by a user via the user interface.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 2 is a message sequence chart illustrating example interactions between elements of the system of FIG. 1.

FIG. 20 is an illustration of an example GUI for receiving a selection of a drug regimen.

FIG. 21A is an illustration of an example GUI for displaying procedure data.

FIG. 21B is an illustration of an example GUI for modifying parameters of a procedure.

FIG. 22A is an illustration of an example GUI for displaying organization data for multiple procedures.

FIG. 22B is an illustration of an example GUI for modifying parameters of an organization.

FIG. 23 is an illustration of an example GUI for displaying multiple procedures.

In the drawings, reference numbers may be reused to identify similar and/or identical elements.

DETAILED DESCRIPTION

Real-Time Automated Request Processing System

Figure 1:
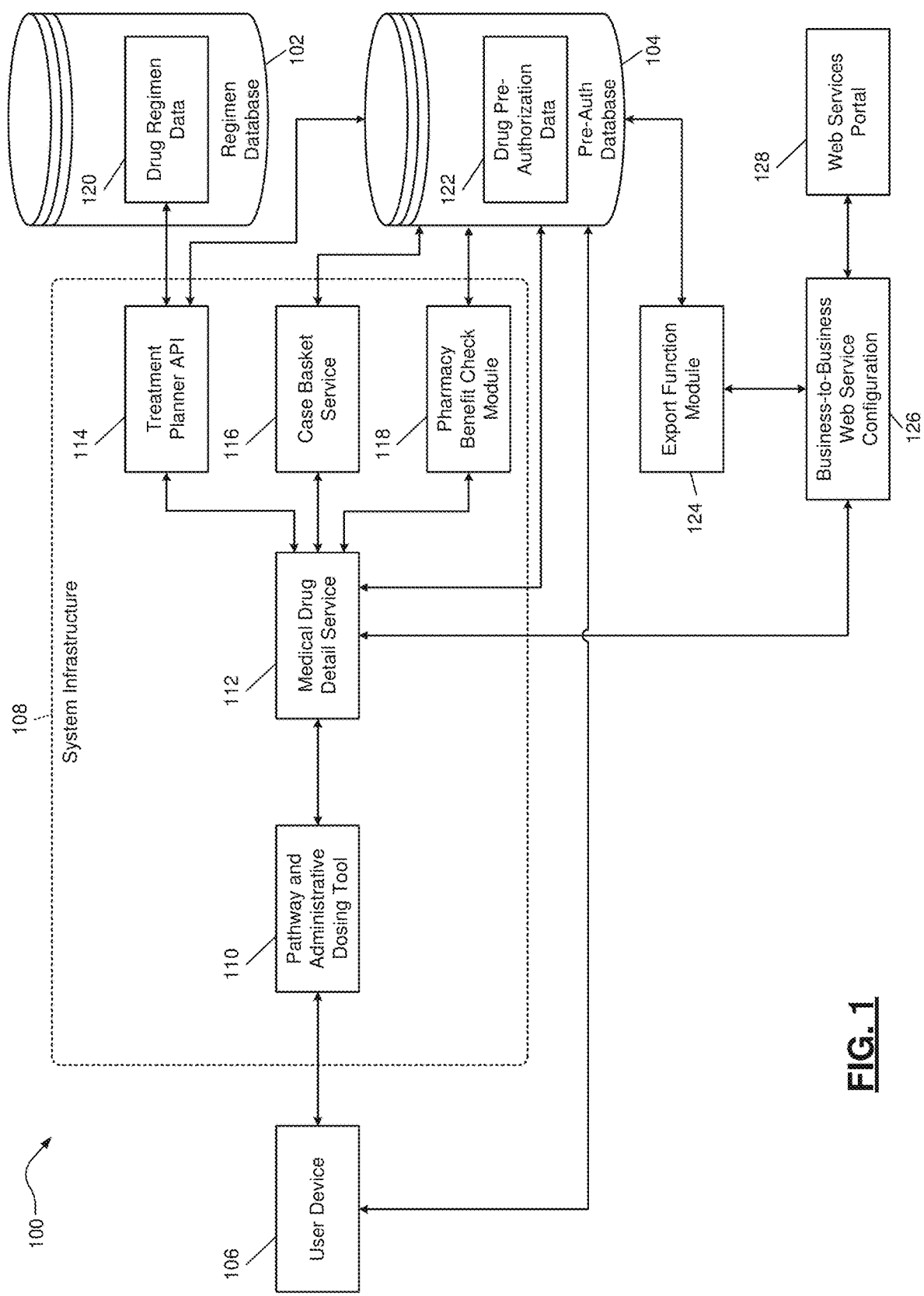
FIG. 1 is a functional block diagram of a system for real-time automated request processing using application programming interfaces.

FIG. 1 is a functional block diagram of an example system 100 for real-time automated request processing using application programming interface, which includes a regimen database 102, a pre-authorization database 104, and a system infrastructure 108. While the system 100 is generally described as being deployed in a computer network system, the regimen database 102, the pre-authorization database 104, and the system infrastructure 108, and/or other components of the system 100, may otherwise be deployed (for example, as a standalone computer setup). The system 100 may include a desktop computer, a laptop computer, a tablet, a smartphone, etc.

As shown in FIG. 1, the regimen database 102 stores drug regimen data 120, and the pre-authorization database 104 stores drug pre-authorization data 122. In various implementations, the regimen database 102 and the pre-authorization database 104 may store other types of data as well. The drug regimen data 120 and the drug pre-authorization data 122 may be located in different physical memories within the regimen database 102 and/or the pre-authorization database 104, such as different random access memory (RAM), read-only memory (ROM), a non-volatile hard disk or flash memory, etc. In some implementations, the drug regimen data 120 and the drug pre-authorization data 122 may be located in the same memory (such as in different address ranges of the same memory). In various implementations, the drug regimen data 120 and the drug pre-authorization data 122 may each be stored as structured data in any suitable type of data store.

The system infrastructure 108 may include one or more modules, services, tools, application programming interfaces (APIs) and so on, for performing real-time automated request processing. For example, FIG. 1 illustrates a treatment planner API 114 in communication with the regimen database 102 and the pre-authorization database 104, a case basket service 116 in communication with the pre-authorization database 104, and a pharmacy benefit check module in communication with the pre-authorization database 104. A medical drug detail service 112 is in communication with the treatment planner API 114, the case basket service 116, and the pharmacy benefit check module 118.

As shown in FIG. 1, the system infrastructure 108 includes a pathway and administrative dosing tool 110 that interfaces between the medical drug detail service 112 and the user device 106. For example, a user may access the system infrastructure 108 via the user device 106 to provide clinical responses for selecting a drug regimen, to request authorization of a drug regimen, to develop control pathways for selecting drug regimens, and so on. The user device 106 may include any suitable user device for displaying text and receiving input from a user, including a desktop computer, a laptop computer, a tablet, a smartphone, etc. The user device 106 may access the system infrastructure 108 (or regimen database 102 or pre-authorization database 104) directly, or may access the system infrastructure 108 (or regimen database 102 or pre-authorization database 104) through one or more networks. Example networks may include a wireless network, a local area network (LAN), the Internet, a cellular network, etc.

In various implementations, the system 100 includes an export function module 124, a business-to-business web service configuration 126, and a web services portal 128. For example, the export function module 124 may communicate between the pre-authorization database 104 and the business-to-business web service configuration 126. The business-to-business web service configuration 126 may communicate between the medical drug detail service 112, the export function module 124, and the web services portal 128.

FIG. 2 is a message sequence chart illustrating example interactions between the user device 106, the pathway and administrative dosing tool 110, the medical drug detail service 112, the pharmacy benefit check module 118, the case basket service 116, and the web services portal 128. As shown in FIG. 2, the user device 106 transmits a drug authorization request to the pathway and administrative dosing tool 110, at line 204. At line 208, the pathway and administrative dosing tool 110 initiates pathway workflows specific to the request. For example, the pathway and administrative dosing tool 110 may select automated control pathways that correspond to clinical responses provided by the user via the user device 106 in the drug authorization request. An automated control pathway may execute automatically without receiving any user input, or may optionally receive user input. For example, an automated control pathway may interactively solicit information regarding a patient's condition from a user (such as a medical oncology pathway), and use an automated algorithm to determine and present the appropriate oncology treatment regimens to the user based on the collected information regarding the patient's condition.

At line 212, the pathway and administrative dosing tool 110 supplies dosage information to the medical drug detail service 112. The supplied dosage information may include, for example, information about specified doses of multiple drugs within a drug regimen corresponding to the drug authorization request. At line 216, the medical drug detail service 112 checks the pharmacy benefit status of the request via the pharmacy benefit check module 118, and returns a status determination to the medical drug detail service 112 at line 220.

The medical drug detail service 112 supplies a status determination to the pathway and administrative dosing tool 110, at line 224. At line 228, the pathway and administrative dosing tool 110 performs a pathway calculation specific to the request. For example, the pathway and administrative dosing tool 110 may use information obtained from the pharmacy benefit check module 118 and/or the medical drug detail service 112, to implement one or more automated control pathways related to the drug authorization request received via the user device 106.

At line 232, the pathway and administrative dosing tool 110 supplies pathway calculations and completion data to the medical drug detail service 112. The medical drug detail service 112 then saves pathway calculations for the requested drugs of the regimen at 236, and optionally saves corresponding dosage information, via the case basket service 116. The medical drug detail service 112 determines a request source type at line 240, such as whether the request is pharmacy benefit coverage request or a medical benefit coverage request. At line 244, the medical drug detail service 112 exports data using a web service and/or batch, according to the request source type.

Authorization Request Processing

Figure 3A:
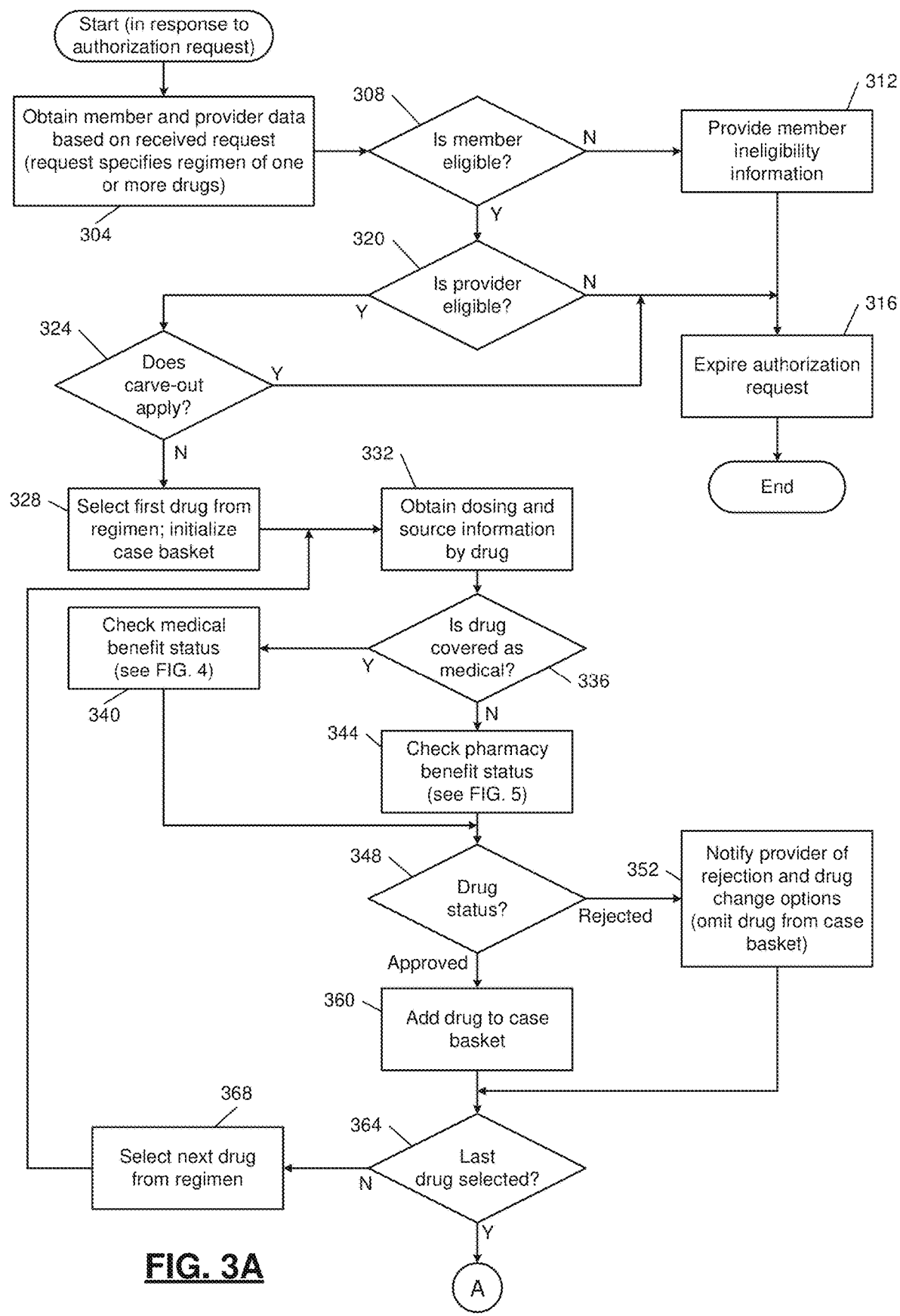
FIGS. 3A and 3B are flowcharts illustrating an example method of processing an authorization request.
Figure 3B:
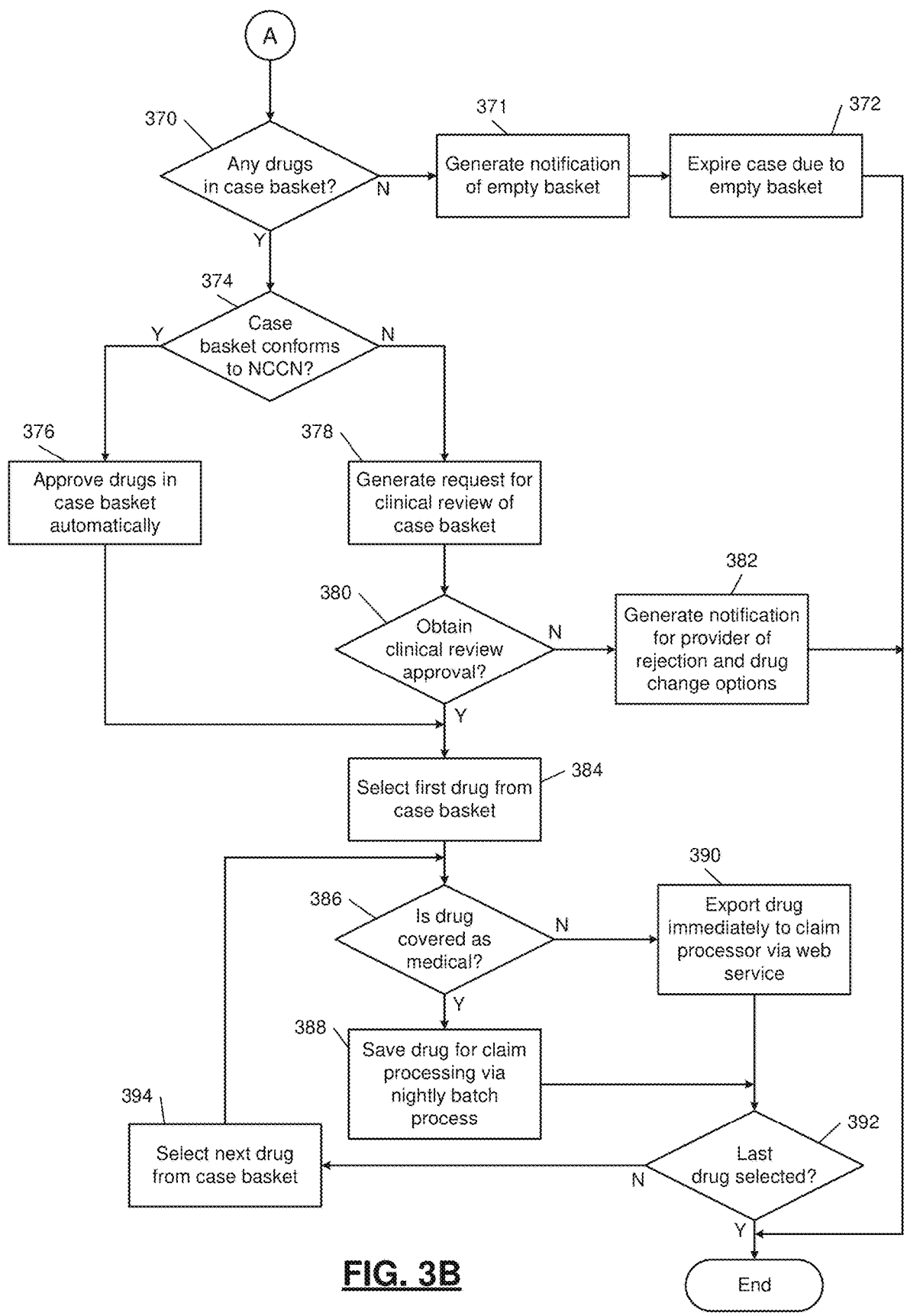

FIGS. 3A and 3B are flowcharts illustrating an example method of processing an authorization request. Control begins in response to a received authorization request, by obtaining member and provider data based on the received request, at 304. For example, the request may specify a regimen of one or more drugs. At 308, control determines whether a member included in the request is eligible for drug authorization. For example, control may determine whether the member has prescription drug coverage, medical coverage, pharmacy benefit coverage, and so on. If not, control proceeds to 312 to provide member ineligibility information, such as providing a notification to the user device 106 that the member is not eligible for drug authorization. Control may then expire the authorization request at 316, due to the ineligible member.

If control determines at 308 that the member is eligible, control proceeds to 320 to determine whether a health plan provider associated with the request is eligible. For example, control may determine whether the provider requesting authorization of the drug regimen is enrolled for accepting medical coverage, pharmacy benefit coverage, prescription drug coverage, and so on. If not, control expires the authorization request at 316 due to an ineligible provider.

If control determines at 320 that the provider is eligible, control proceeds to 324 to determine whether a carve-out rule applies. For example, specific carve-out rules may apply in unique situations that require manual handling of the drug authorization request. If control determines at 324 that a carve-out does apply, control proceeds to 316 to expire the authorization request due to the carve-out rule.

Figure 4:
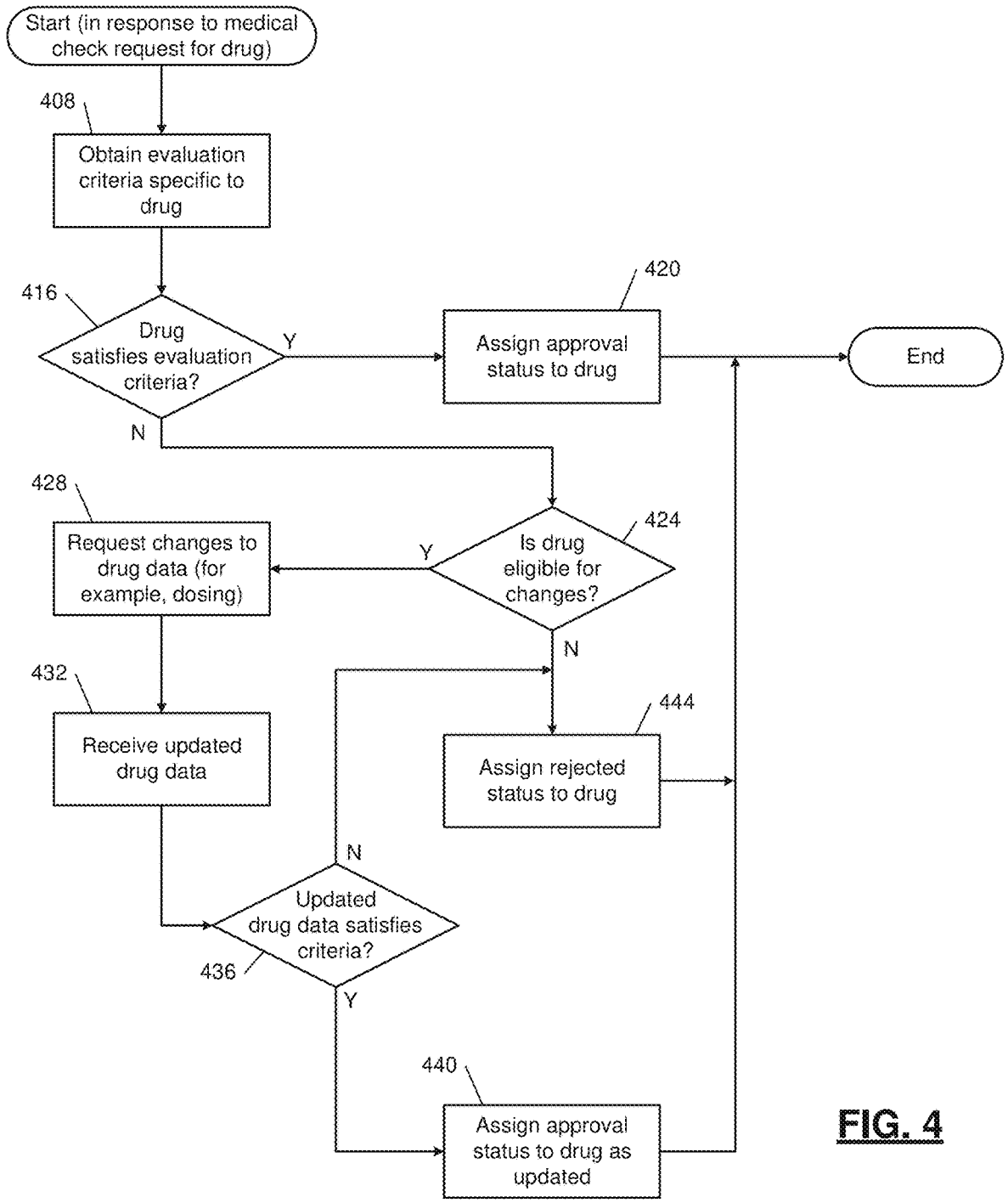
FIG. 4 is a flowchart illustrating an example method of processing a medical check request.

When control determines that a carve-out does not apply at 324, control proceeds to 328 to select the first drug from the regimen and initialize the case basket. At 332, control obtains dosing and source information by drug. For example, control may select a first drug from the regimen and obtain dosing information for that drug according to the authorization request. At 336, control determines whether the drug is covered under medical benefit coverage. If so, control proceeds to 340 to check medical benefit status. One example process for checking medical benefit status is illustrated in FIG. 4, and described further below.

Figure 5:
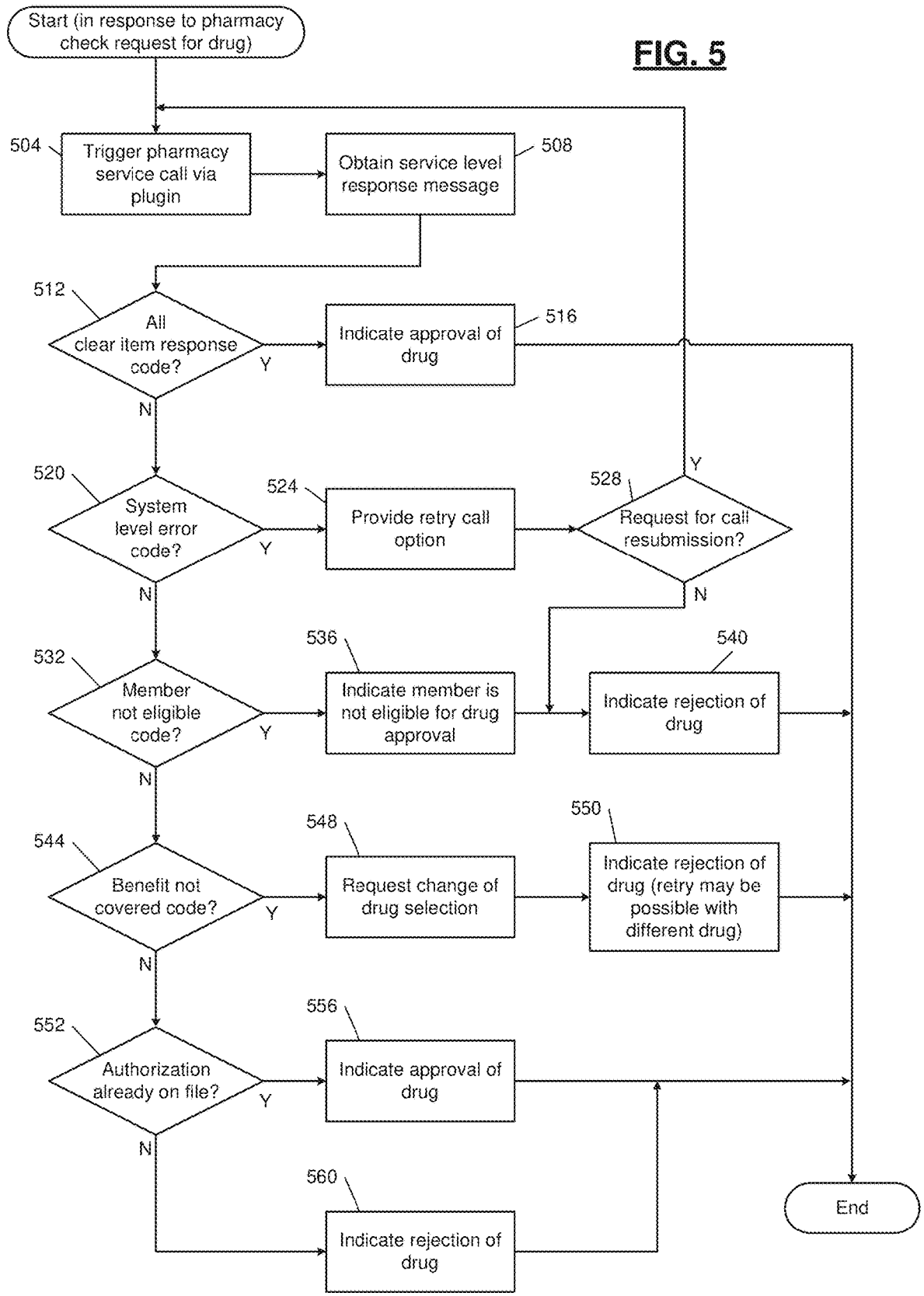
FIG. 5 is a flowchart illustrating an example method of processing a pharmacy check request.

If control determines at 336 that the drug is not covered under medical benefits, control proceeds to 344 to check pharmacy benefit status. An example process for checking pharmacy benefit status is illustrated in FIG. 5 and described further below. After checking the medical benefit status at 340, or checking the pharmacy benefit status at 344, control proceeds to 348 to determine the status of the drug. If the drug status is rejected, control proceeds to 352 to notify the provider of the rejection, and optionally presents the provider with an opportunity to make changes to the drug in the authorization request. In this case, the drug may be omitted from the case basket.

When the drug status is approved at 348, control proceeds to 360 to add the drug to the case basket. After adding the drug to the case basket at 360, or notifying of the provider of the rejection at 352, control proceeds to 364 to determine whether the last drug has been selected. If the last drug has not been selected at 364, control proceeds to 368 to select the next drug from the regimen, and then proceeds to 332 to obtain dosing and source information for the next selected drug.

After selecting last drug at 364, control proceeds to 370 to determine whether any drugs were added to the case basket (for example, to make sure that the basket is not empty due to drug exclusions). If there are not any drugs in the case basket, control generates a notification of the empty basket at 371, and then expires the case due to the empty basket at 372. If control determines at 370 that at least one drug exists in the case basket, control proceeds to 374 to determine whether the case basket conforms to NCCN. If so, control may approve the drug(s) in the case basket automatically at 376.

If control determines at 374 that the case basket is not conformed to NCCN, control proceeds to 378 to generate a request for a clinical review of the case basket. Control then determines at 380 whether a clinical review approval is obtained. For example, control may request an administrator to manually review the case basket when it does not conform to in CCN, and if the administrator provides a denial, control proceeds to 382 to generate a notification for the provider of the rejection. Control may optionally provide drug change options that the provider could use to make changes the drug authorization request, in order to have the requested drug regimen be approved.

When a clinical review approval is obtained at 380, control proceeds to 384 to select the first drug from the case basket. Control then determines at 386 whether the drug is covered as a medical benefit. If not, control proceeds to 390 to export the drug to the claim processor via a web service. This export process may occur immediately, on a schedule within a specified time period, and so on. If control determines that the drug is covered as a medical benefit at 386, control proceeds to 388 to save the drug for claim processing via, for example, a nightly batch process. Control then determines at 392 whether the last drug has been selected. If not, control selects the next drug from the case basket at 394, and returns to 386 to determine whether the next drug is covered as a medical benefit. Once the last drug is selected 392, the drug authorization process ends for that drug regimen.

FIG. 4 is a flowchart illustrating an example method of processing a medical check request. Control may start the process in response to a medical check request for the drug, such as the request at 340 in FIG. 3A. At 408, control obtains evaluation criteria specific to the drug. If the drug satisfies evaluation criteria at 416, control assigns an approval to the drug at 420. For example, the evaluation criteria may specify one or more parameters that must be met for a drug to be authorized under a medical benefit coverage.

If the drug does not satisfy the evaluation criteria at 416, control proceeds to 424 to determine whether the drug is eligible for changes. If the drug is not eligible for changes, control assigns a rejected status to the drug at 444. If control determines at 424 that the drug is eligible for changes, control proceeds to 428 to request changes to the drug data. For example, control may allow the user to change dosing information for the drug within the regimen, or make other suitable modifications in order to allow the drug to be authorized.

At 432, control receives updated drug data, such as from the provider via the user device 106. At 436, control determines whether the updated drug data satisfies the evaluation criteria. If not, control assigns a rejected status to the drug at 444. If control determines at 436 that the updated drug data satisfies the evaluation criteria, control assigns an approval status to the drug as updated at 440.

FIG. 5 is a flowchart illustrating an example method of processing a pharmacy check request. Control may start in response to a pharmacy check request for a drug, such as in response to the request for a pharmacy check at 344 from FIG. 3A. At 504, control triggers a pharmacy service call via a plug-in. Control then obtains a service level response message at 508.

At 512, control determines whether the service level response message includes an all clear item response code. If so, control indicates an approval of the drug at 516. If control determines that the serviceable response message does not include an all clear item response code at 512, control proceeds to 520 to determine whether the service level response message includes a system error code.

If control determines at 520 that the service level response message includes a system level error code, control proceeds to 524 to provide a retry call option. Control then determines whether a request for call resubmission was received, at 528. If so, control returns to 504 to trigger the pharmacy service call via plug-in, to obtain another service level response message at 508. If control determines at 528 that a request for call resubmission was not received, such as the user not wishing to resubmit the request, control proceeds to 540 to indicate a rejection of the drug.

If a system level error code is not present in the obtained service level response message at 520, control proceeds to 532 to determine whether a member not eligible code is present. If so, control proceeds to 536 to indicate that the member is not eligible for drug approval, and then indicates a rejection of the drug at 540. If control determines that the obtained service level response message does not include a member not eligible code at 532, control proceeds to 544 to determine whether the service level response message includes a benefit not covered code.

When the service level response message does not include the benefit not covered code, control proceeds to 548 to request a change in the drug selection. Control then indicates a rejection of the drug at 550, where a retry may be possible with a different drug. For example, control may reject a current drug as not being covered by member benefits, while control also provides one or more other suggested drugs that are covered under member benefits and could potentially be selected by the provider to obtain an authorization.

If control determines at 544 that the service level response message does not include a benefit not covered code, control proceeds to 552 to determine whether an authorization for the drug is already on file. If an authorization is already on file, control proceeds to 556 to indicate an approval of the drug. If an authorization is not already on file, control indicates a rejection of the drug at 560. In various implementations, control may use other catchall provisions when specific codes are not included in the obtained service level response message, control may check codes of the service level response message in different orders, control may look for codes other than those shown in FIG. 5, and so on.

Figure 6:
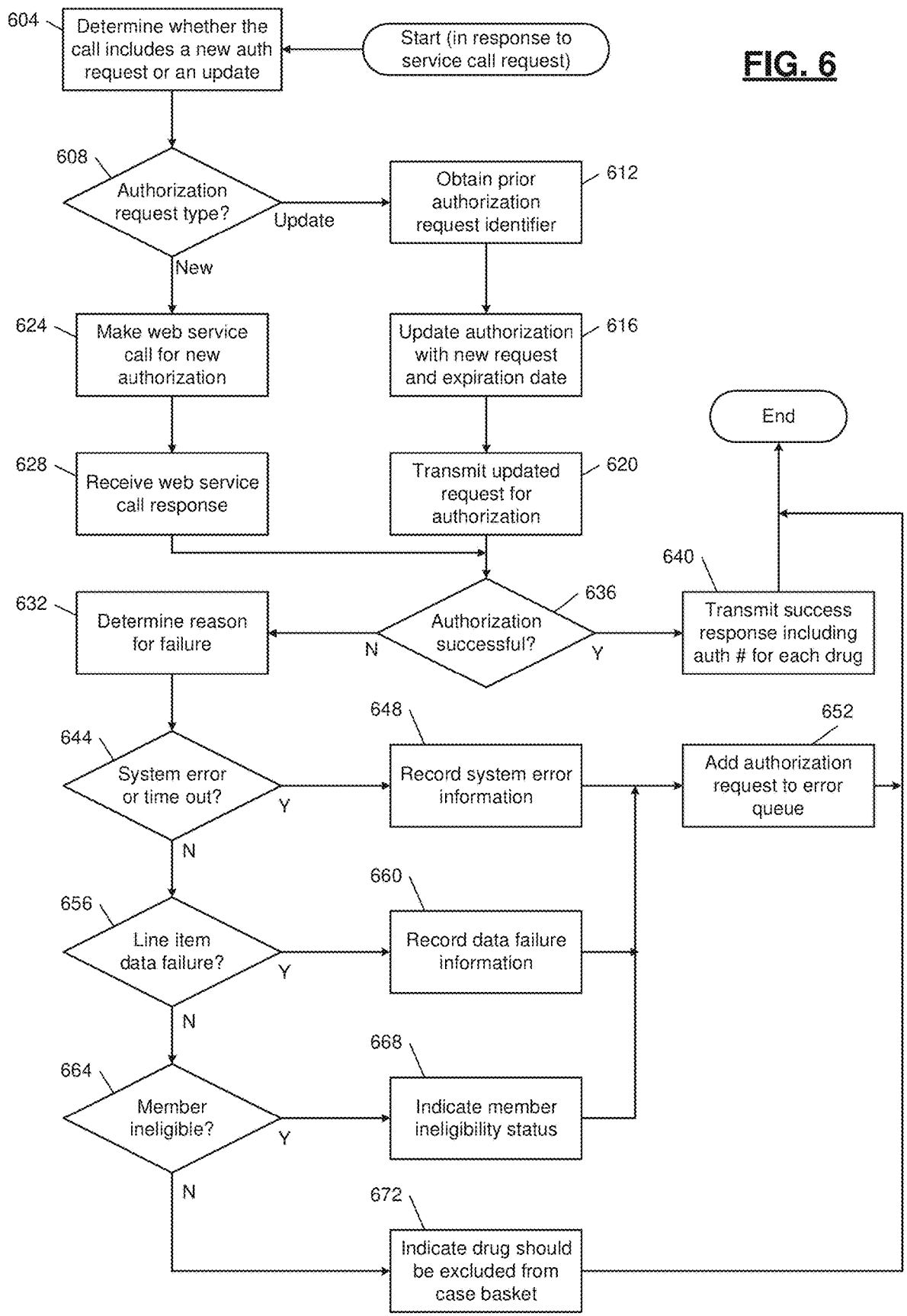
FIG. 6 is a flowchart illustrating an example method of processing a service call request.

FIG. 6 is a flowchart illustrating an example method of processing a service call request. Control may begin the process in response to a service call request, by determining whether a call includes a new authorization request or an update at 604. If the authorization request type is an updated authorization at 608, control obtains a prior authorization request identifier at 612, and updates the authorization with the new request and expiration date at 616. Control then transmits the updated request for authorization at 620.

If control determines at 608 that the authorization request type is new, control makes a web service call for a new authorization at 624. Control then receives the web service call response at 628. At 636, control determines whether the authorization was successful. If so, control transmits a success response including the authorization number for each drug, at 640.

When the authorization is not successful at 636, control proceeds to 632 to determine a reason for the failure. If a system error timeout occurred at 644, control records the system error information at 648, and then adds the authorization request to an error queue at 652. For example, the error queue may include authorization requests that were not able to be processed in an automatic manner, and require manual review by an administrator.

If control determines at 644 that the reason for the authorization failure is not due to a system error timeout, control proceeds to 656 to determine whether the reason for the authorization failure was due to a line item data failure. If so, control records the data failure information at 660, and then adds the authorization request the error queue at 652. If control determines at 656 that the unsuccessful authorization is not due to a line item data failure, control proceeds to 664 to determine whether the reason for failure is an ineligible member.

If the reason for failure at 664 is eligible member, control indicates the member and eligibility status at 668, and adds the authorization request to the error queue at 652. If control determines at 664 that the failure for authorization is not due to member eligibility, control proceeds to 672 to indicate that the drug should be excluded from the case basket. This may be considered as a catchall provision if the authorization reason for failure does not correspond to predefined categories. In various implementations, other reasons for failure may be checked, other catchall actions may be implemented, and so on.

In various implementations, after a health care provider (such as a physician or pharmacist) enters clinical information via a web portal, the provider may be presented with a list of recommended drug regimens to treat a patient based on the entered clinical information, as well as the option to build a custom request from a list of individual drugs, using an automated control pathway. The selected drugs may be populated on a dosing screen within the automated control pathways with configurable dosing values.

In various implementations, selected drugs may be added to a case basket that includes one or more drugs of a drug regimen. For example, a set of real-time rules may be run on the selected drugs (where the rules may be different for medical benefit requested drugs and pharmacy benefit requested drugs), and the automated control pathway may determine whether each drug should be added to the case basket.

If the drug regimen is an NCCN recommended regimen, all drugs in the case basket may be automatically approved. Custom drug requests may be sent to a doctor or other administrator for clinical review. The reviewer may have the ability to open the automated control pathway and make changes to the clinical responses and selected drugs as needed.

Development Environment for Automated Control Pathways

Figure 7:
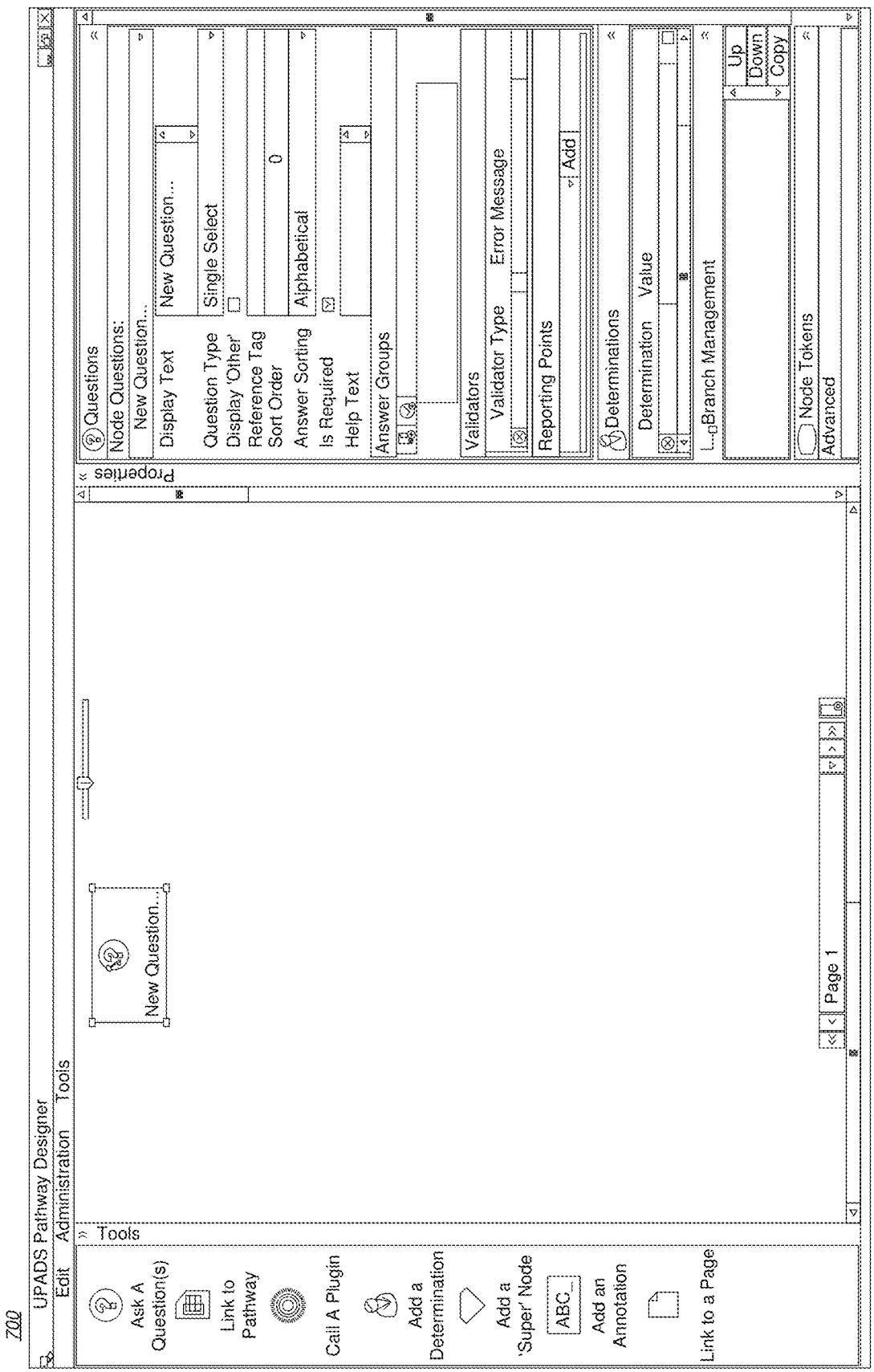
FIG. 7 is an example graphical user interface (GUI) of a development environment for generation of automated control pathways.

FIG. 7 is an example graphical user interface (GUI) of a development environment for generation of automated control pathways. In various implementations, the development environment may use building blocks and logic to design automated control pathways in accordance with, for example, national comprehensive cancer network (NCCN) evidence based criteria, centers for Medicare and Medicaid services (CMS), state healthcare criteria, and health plan specific policies and criteria.

In response to starting development of a new automated control pathway, a user may be presented with the screen 700 illustrated in FIG. 7. The initial screen 700 is divided into three sections. The large center section is a palette area or working area where the pathway is displayed, showing the relationship between different elements of the pathway.

The left side of the screen 700 includes a graphical user interface in a navigation bar, which includes programming elements that may be referred to as building blocks. When you select one of the elements and drag it into the palette area, the element may be referred to as a pathway node. The right side of the screen 700 includes a section that displays related properties of the currently selected node.

FIG. 7 illustrates a number or example elements that may be selected by a user. The question element (referred to as Ask A Question) may be used to prompt a user with a question. For example, the control pathway illustrated on the screen 700 may be used by a provider to navigate submission of clinical responses to determine one or more appropriate drug regimens for treating a patient. The question element may produce a screen to the provider that asks the provider a specified question (or multiple questions) to receive clinical responses from the provider.

The pathway element (referred to as Link to Pathway) enables the pathway that is currently being written to be linked to another pathway. The plugin element (referred to as Call a Plugin) may call to software outside of the automated control pathway system. For example, the pathway element may be used to obtain database information from another system, to perform advanced calculations, and so on. If there is a difference in criteria for a certain test based on a member's age, the patient demographic plugin may be called by the plug in element (for example, to obtain the patient's demographic data from another database).

The determination element (referred to as Add a Determination) may be used to conclude a pathway with either a certification or denial, include a message within the pathway, or help organize a pathway. The annotation element (referred to as Add an Annotation) may also be used to include a message within the pathway or help to organize a pathway. The page element (referred to as Link to a Page) may be used to connect multiple pages of pathways within one pathway design. This element may be used when the pathway has several components or is more complex or lengthy than other pathways.

As an example, a user may drag the question element into the blank space of the screen 700 to place the question element at a desired location. After the user clicks on the question element at its location, a properties box will open on the right side of the screen 700. As shown in FIG. 7, the properties box includes a New Question field that allows the user to create a new question for the element, and a Display Text field that contains the text that will appear on the outward facing UI to a provider when the provider reaches this particular question element node during running of the automated pathway.

The "Question Type" field may be used to manage the question element as providing an option for a single select, a multiple select, a yes or no, or a message to the user. For example, this field may specify the type of question that will be presented to a provider on a UI during use of the automated control pathway. The multiple select question type may be used when more than one selection is needed to certify an examination. The data question type may be used to prompt the provider to pick a date from a calendar. The free text question type may present a one line text box that allows the user to type in a limited amount of characters. The numeric question type may be used to obtain a numeric answer such as a lab value. A yes and no question type will allow the provider to select between either a yes answer or a no answer. A note question type may allow the user to type in significantly more information than the free text box.

The "Display Other" field may be used for numeric type questions, and the "Reference Tag" field may be a label supplied to the question element when the question element is listed for use in branch logic. The "Sort Order" field may be used when there are multiple questions, such that the questions will appear in the order of the number assigned to the Sort Order field. The pathway designer automatically assigns these values, which may be important when questions are added or deleted. The "Answer Sorting" field tells the automated pathway designer how the answer group of questions should appear, such as alphabetical or other sorting techniques.

The "Is Required" field may determine whether the user will be required to answer the question before moving on in the automated control pathways UI. If the developer wants to allow the provider to skip the question, the box should be manually unchecked. The "Help Text" field is a short comment to help the provider understand what is being asked, and the "Answer Groups" field lists that answer choices that the provider can select from during use of the automated control pathway. For example, answer groups may allow for use of logic to tell the pathway how to behave based on the answer choice selected by the provider. The "Validators" field may set rules for an answer, such as requiring a decimal point. The example properties shown in FIG. 7 are for purposes of illustration only, and other implementations may include other suitable properties for each element.

Figure 8:
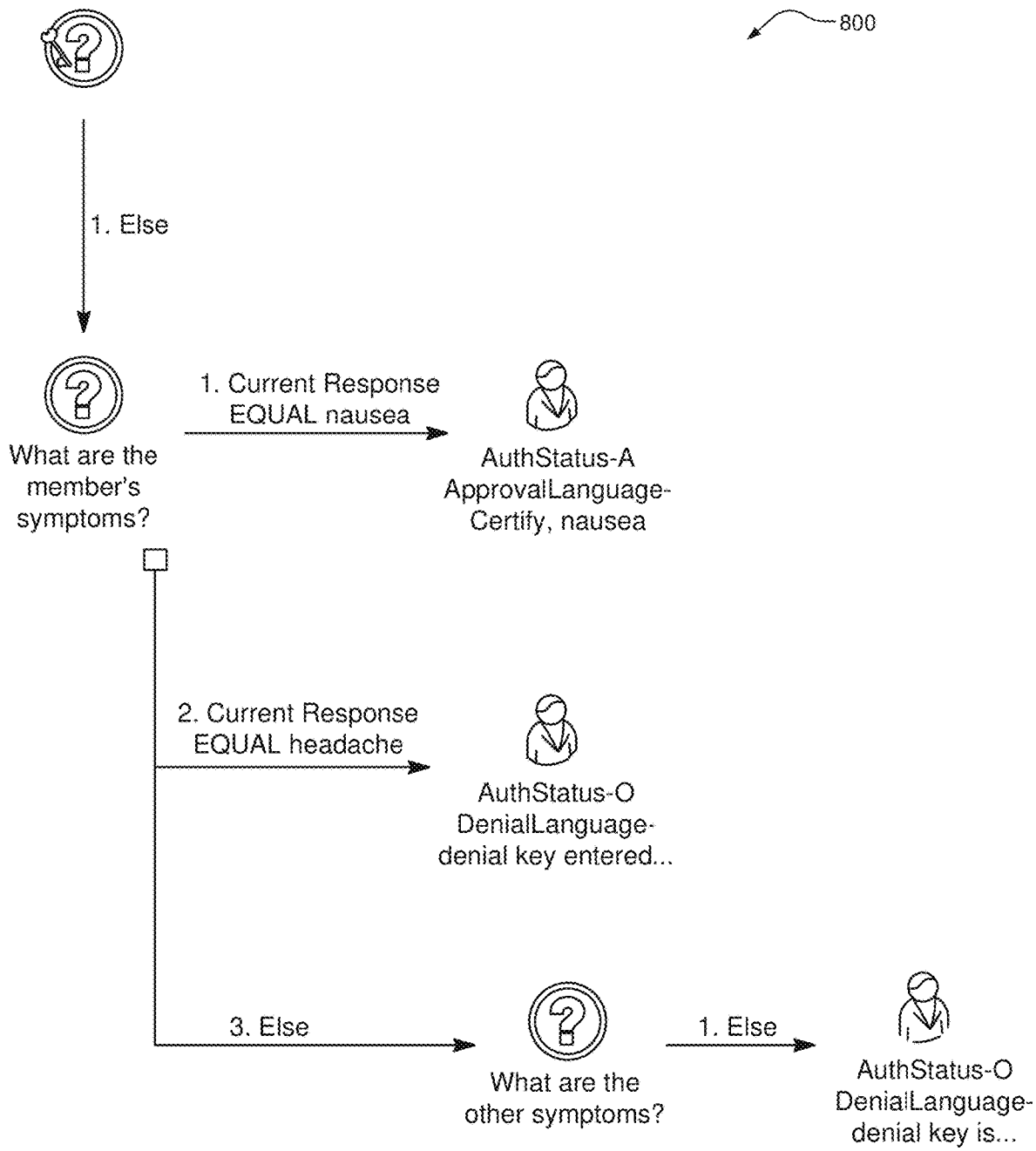
FIG. 8 is an illustration of an example automated control pathway generated via the GUI of FIG. 7.

FIG. 8 is an illustration of an example automated control pathway 800 generated via the GUI of FIG. 7. As shown in FIG. 8, multiple programming branches connect the building blocks of the pathway together. The conditional logic applied to each branch determines how the pathway will behave. For example, if the pathway prompts a provider with a question of "What are the member's symptoms?" and receives a response from the provider equal to "nausea", the pathway takes branch number 1 and supplies an approval.

In various implementations, the control pathway may review branches in the order of a numerical sequence of the branches. For example, if the provider response is not equal to nausea, the pathway may next check whether the provider response is equal to "headache" at branch number 2. If so, the pathway may issue a denial as shown in FIG. 8. In this example, the drug may be approved if the patient has a symptom of nausea, but not if the patient has a symptom of headache.

An Else branch may be used to for the pathway if no prior branches are met. In FIG. 8, the Else branch may ask the provider what other symptoms are if nausea or headache was not submitted, and possibly issue a denial depending on the other symptoms (for example, if nausea is the only symptom for which the drug may be authorized).

As shown in FIG. 8, branches 1 and 2 end in a determination element. In various implementations, the determination element may have a value of "A" for approval, or "O" for denial. Alternatively, the determination element may have no value when it is being used as a place holder or to help organize a pathway. If a determination element is assigned a value of A to indicate approval, the developer may enter approval language in the element properties to specify language that will appear in a journal note with the approval. If a determination element is assigned a value of O to indicate a denial, a denial key may be assigned (for example, from a unique denial spreadsheet created for the pathway), and the case may go to a medical review. In various implementations, a developer may specify one or more data points at different locations in the pathway to collect data, which may be used for review of cases, for future development of pathways, and so on.

In various implementations, error and warning messages may be used to inform the developer of when there is an issue with the pathway that may cause an error for a provider. For example, a minor warning (sometimes referred to as a yellow warning) may still allow a pathway to be saved, but suggests that the pathway may not perform as expected. It is generally recommended to correct minor warnings, although there may be instances where a minor warning occurs even though there is no actual error in the pathway (such as when a token is manually entered from a separate pathway).

As an example of a minor warning, a question element may ask if the provider wants to select option A or option B. The pathway may first check if the provider selected option A, and then move on to an Else branch before checking for option B. In this example, the developer may be allowed to save the pathway because it technically can run without causing a fault, but the system may issue the minor warning to let the developer know that option B is never checked.

A major warning (sometimes referred to as a red warning) may prevent the pathway from being saved until the error is fixed. For example, if a question element is provided with a single select question property specified, but the developer has not entered any answers in the list for the question element, the provider will not be able to select any answer because the list is empty. In this example, a major warning or error may be issued that prevents saving the pathway until the developer adds at least one answer to the list.

In various implementations, the control pathways may be developed in multiple environments, including a pathway designer test harness environment, a development environment, and an integration environment. When changes are made in the pathway designer and saved, the changes may be reflected in the development environment immediately. The development environment may be used to test the pathway to determine how it will behave when used by providers, and to verify correct denials.

The integration environment may more closely reflect a live environment that is used by providers. For example, the integration environment may be used to evaluate pathway performance for different cases. In various implementations, the integration environment may be updated less frequently than the development environment or pathway designer (such as every week, every night, every fifteen minutes, and so on), so changes made in the pathway designer may not be immediately available in the integration environment.

Control Pathway Generation Process

Figure 9:
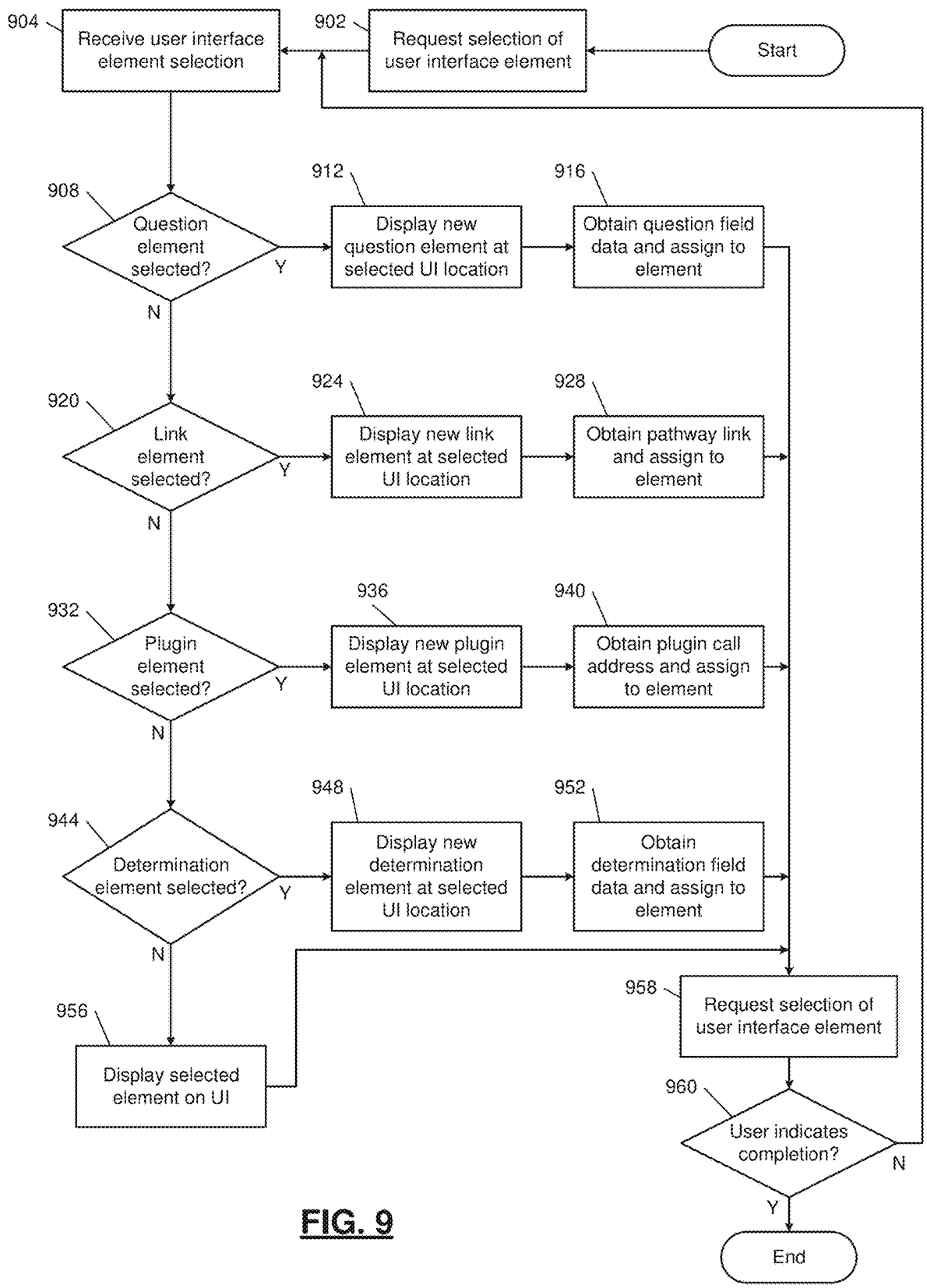
FIG. 9 is a flowchart illustrating an example process of generating different elements of an automated control pathway.

FIG. 9 is a flowchart illustrating an example process of generating different elements of an automated control pathway. Control begins at 902 by requesting selection of a user interface element, and receiving a selection of a user interface elements at 904. For example, multiple user interface elements (such as icons) maybe displayed on a screen, and the user may select one of the interface elements to place in the development environment. An example screen including multiple user interface elements is illustrated in FIG. 7.

At 908, control determines whether a question element was selected. If so, control proceeds to 912 to display a new question element at a selected UI location. Control then obtains question field data and assigns the obtained data to the element, at 916. For example, after a user selects the question element icon and places it at a location in the development environment screen, the user may select the Edit button to fill out relevant data fields associated with the question element, which are then assigned to the questions element in the control pathways development environment.

If control determines at 908 that the question element is not selected, control proceeds to 920 to determine whether a link element is selected. If so, control displays a new link element at a selected UI location, at 924. Control then obtains a pathway link at 928 and assigns the obtained pathway link to the new element. For example, a user may select a pathway link icon as displayed in the example of FIG. 7, and place the selected pathway link icon within the displayed development environment space. The user then chooses a control pathway for linking to the new element, and that pathway link is assigned to the new element in storage.

If control determines at 920 that a link element was not selected, control proceeds to 932 to determine whether a plug-in element was selected. If so, control displays a new plug-in element at the selected location, at 936. Control then obtains a plug-in call address at 940, and assigns the plug-in call address to the element. For example, the user may select a plug-in element icon from the example screen of FIG. 7, and place the plug-in element at a desired location in the development environment space. The user may then provide an address for the plug-in to call, which is assigned to the plug-in element in storage.

If a plug-in element is not selected 932, control determines whether a determination element was selected at 944. If so, control displays the new determination element at the selected location, at 948. Control then obtains determination field data (which may be input by a user), and assigns the obtained data to the element at 952. For example, a user may select a determination element icon from the example screen of FIG. 7, and place the determination element at a selected location in the development environment. The user may then fill out data fields to specify the type of determination that will be performed by the determination element.

If the user selects a type of element other than the question element, link element, playing element, or determination element, control displays the other selected element on the UI of the development environment, at 956. After displaying each new element and/or assigning appropriate data to each element, control requests selection of another user interface element at 958. For example, control may continue displaying multiple element icons while waiting for the user to make another selection.

If control determines at 960 that the user has indicated the process of generating the automated control pathways is over (for example, by saving the control pathways and exiting the development environment), the process ends. If the user has not indicated that the process is complete, control returns to 904 to another user interface element selection from the user. Although FIG. 9 illustrates control determining whether different elements are selected in a sequential manner, in various implementations control may wait until a user clicks on any one of multiple displayed elements, and then perform functions related to the selected element at that time.

Figure 10:
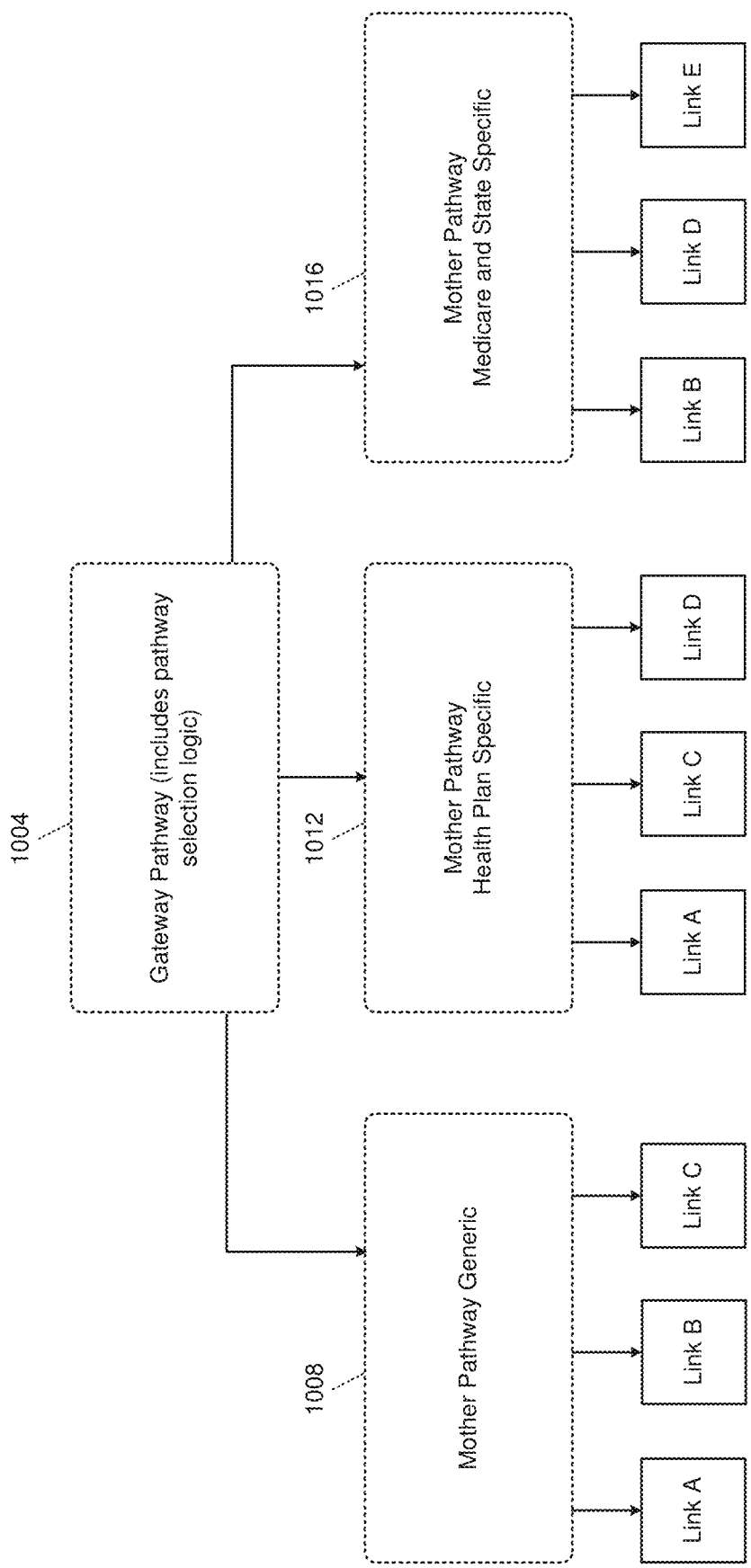
FIG. 10 is a block diagram illustrating example relationships between gateway pathways and different link elements.

FIG. 10 is a block diagram illustrating example relationships between gateway pathways and different link elements. For example, a gateway pathway 1004 may be generic to multiple other types of pathways, and used as an initial starting point to determine which specific pathways should be used for a specific case. As shown in FIG. 10, the gateway pathway 1004 includes pathway selection logic. The pathway selection logic may use clinical responses from a provider, member medical coverage information, or other suitable data, to determine which pathway should be used for a specific case.

For example, the gateway pathway 1004 may determine whether to use a generic mother pathway 1008, a health plan specific mother pathway 1012, or a Medicare and state specific mother pathway 1016. The generic mother pathway 1008 may include pathway links for generic drug authorization determinations, such as Link A, Link B and Link C shown in FIG. 10.

The health plan specific mother pathway 1012 may include links that correspond to different health plans, such as Link A corresponding to a first health plan, Link B corresponding to a second health plan, and Link C corresponding to a third health plan. If a member has coverage under the third health plan, the gateway pathway 1004 may route to the health plan specific mother pathway 1012, which then selects Link C to process the requested drug authorization for the member.

The Medicare and state specific mother pathway 1016 may include links that correspond to different government coverage plans, such as Link B corresponding to a first state health plan, Link D corresponding to a second state health plan, and Link E corresponding to Medicare coverage. If a member has coverage under Medicare, the gateway pathway 1004 may route to the Medicare and state specific mother pathway 1016, which then selects Link E to process the requested drug authorization for the member. The arrangement of generic pathways and links in FIG. 10 is for purposes of illustration only, and various implementations may use other arrangements of generic pathways, other common and individual links for the generic pathways, and so on.

Figure 11:
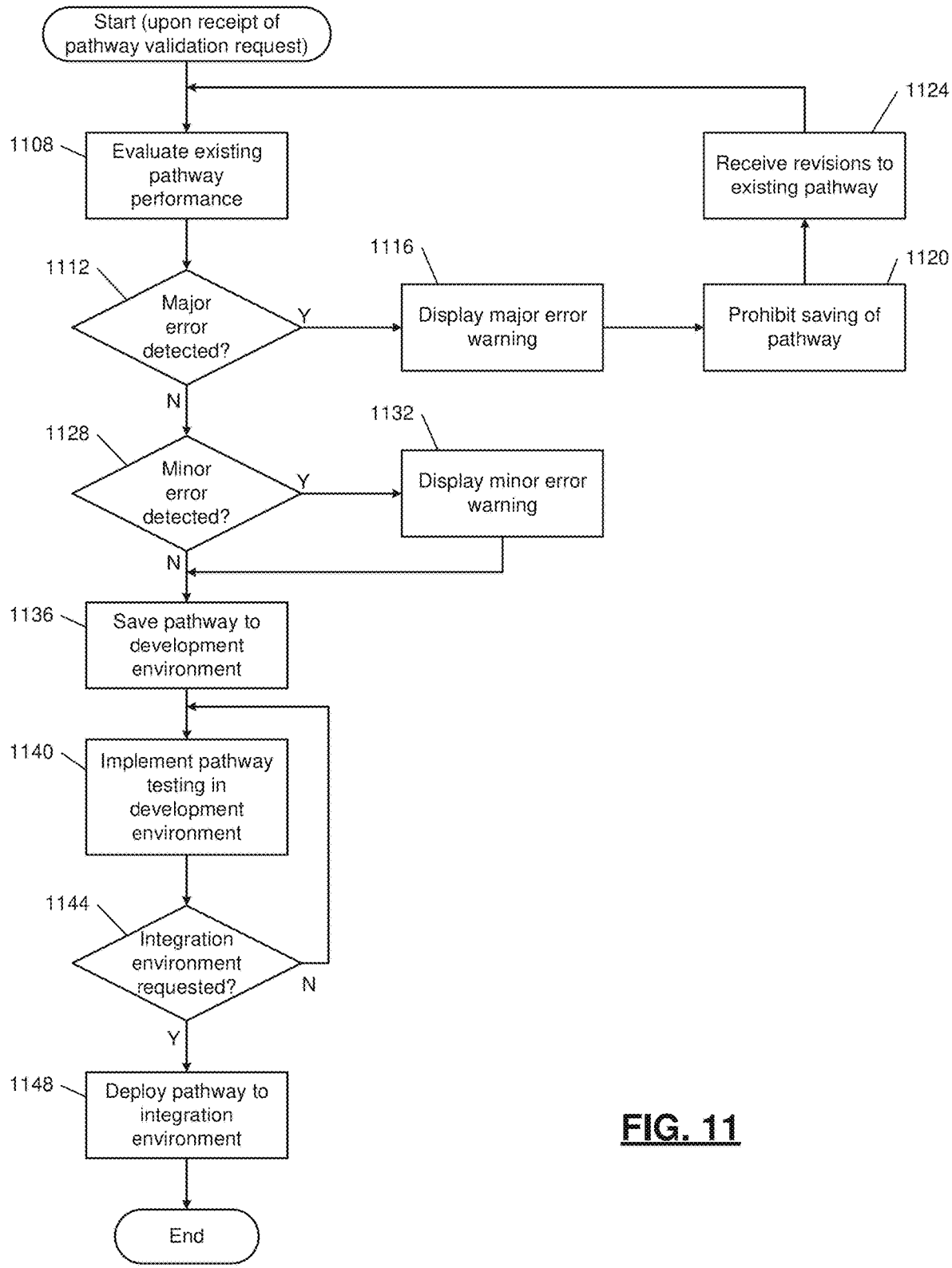
FIG. 11 is a flowchart illustrating an example process of validating an automated control pathway.

FIG. 11 is a flowchart illustrating an example process of validating an automated control pathway. Control begins in response to receiving a pathway validation request, by evaluating existing performance of an existing pathway at 1108. At 1112, control determines whether a major error was detected during the evaluation. If so, control displays a major error warning 1116, and prevents saving of the pathway at 1120. For example, a major error may prevent the pathway from operating properly (such as leading to a process failure error if run in a live environment), so control may prevent the pathway from being saved until the major error is corrected.

Control receives revisions to the existing pathway at 1124, before returning to evaluate performance of the revised pathway at 1108. For example, if the control pathway has a major error that prohibits saving the pathway, the user may be notified or prompted to make changes to the pathway to address the major error. Once the user modifies the existing pathway in an attempt to address the major error, control then reevaluates performance of the revised pathway including the correction at 1108.

If no major errors are detected at 1112, control proceeds to 1128 to determine whether any minor errors are detected. If so, control displays a minor error warning at 1132. The minor error warning may not prohibit saving a pathway, because the pathway can still be operational even with the minor error.

After displaying the minor warning at 1132, or determining that no minor error exists at 1128, control proceeds to 1136 to save the pathway to the development environment. Control then implements the pathway testing in the development environment at 1140. At 1144, control determines whether an integration environment has been requested. If not, control returns to 2140 to continue pathway testing in the development environment.

If control determines at 1144 that the integration environment has been requested by the user, control proceeds to 1148 to deploy the pathway to the integration environment. As described above, several environments may be used for development and implementation of control pathways, including a test harness environment, a development environment and an integration environment. A user may build out the control pathway until it does not contain any major warnings, and save the pathway to the development environment once all major warnings are addressed. The user can then test the pathway in the development environment as much as desired, until the user decides to request promotion of the pathway from the development environment to the integration environment.

Request Processing System Including Application Programming Interfaces

Figure 12:
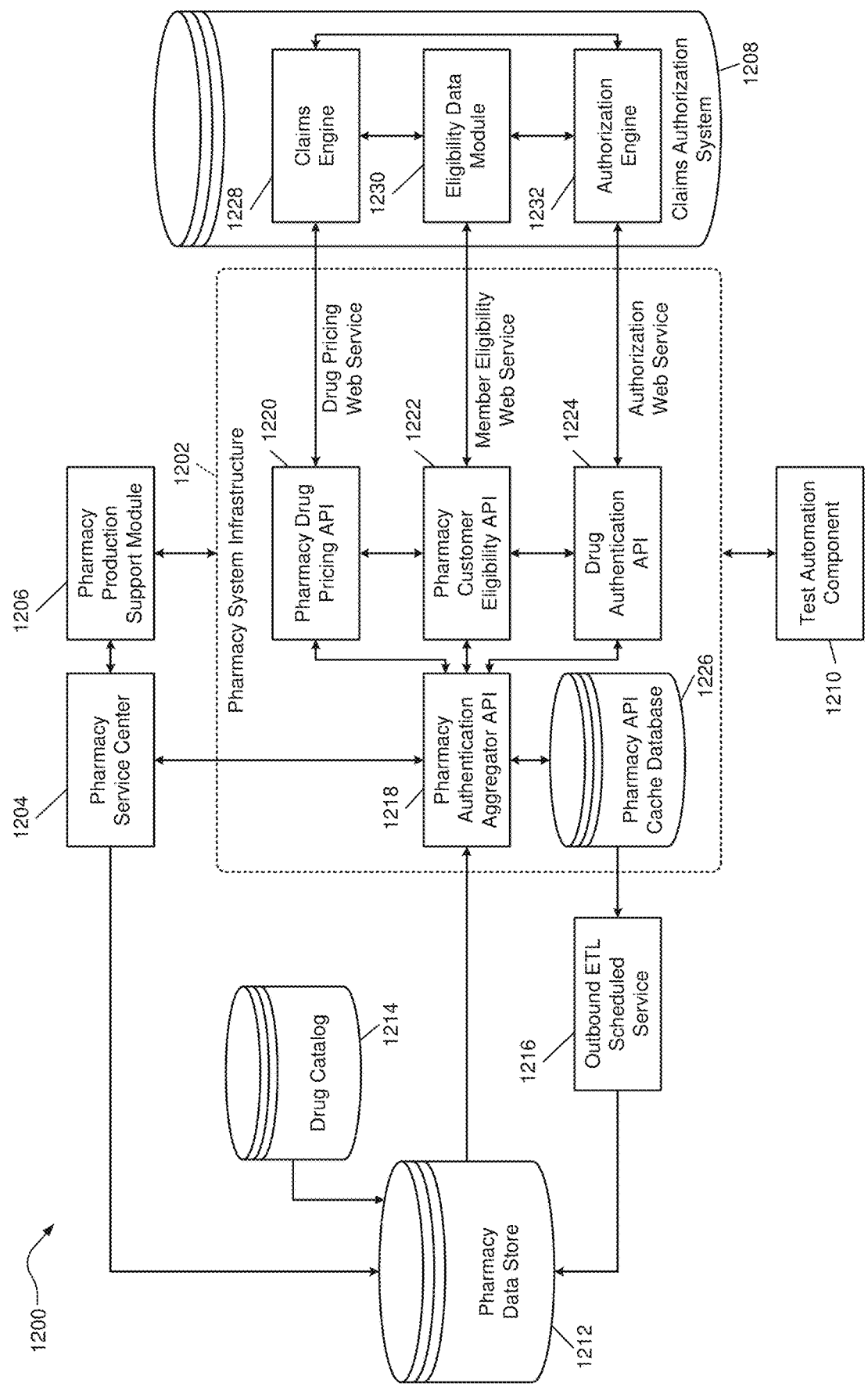
FIG. 12 is a functional block diagram of a system for automated request processing.

FIG. 12 is a functional block diagram of an example system 1200 for automated request processing using application programming interfaces, which includes a pharmacy system infrastructure 1202, and a claims authorization system 1208. While the system 1200 is generally described as being deployed in a computer network system, the pharmacy system infrastructure 1202, the claims authorization system 1208, and/or other components of the system 1200, may otherwise be deployed (for example, as a standalone computer setup). The system 1200 may include a desktop computer, a laptop computer, a tablet, a smartphone, etc.

As shown in FIG. 12, the claims authorization system 1208 incudes a claims engine 1228, an eligibility data module 1230, and an authorization engine 1232. In various implementations, the claims authorization system 1208 may be a third party system that provides validation services for claims processing. The pharmacy system infrastructure 1202 includes a pharmacy drug pricing application programming interface (API) 1220, which communicates with the claims engine 1228 of the claims authorization system 1208 via, for example, a drug pricing web service. The pharmacy system infrastructure 1202 also includes a pharmacy customer eligibility API 1222, which communicates with the eligibility data module 1230 of the claims authorization system 1208 via, for example, a member eligibility web service. The pharmacy system infrastructure 1202 further includes a drug authentication API 1224, which communicates with the authorization engine 1232 of the claims authorization system 1208 via, for example, an authorization web service. One or more firewalls may be implemented between different components of the system to provide different security levels.

The pharmacy system infrastructure 1202 includes a pharmacy API cache database 1226, and a pharmacy authentication aggregator API 1218 that communicates between the pharmacy API cache database 1226 and the pharmacy drug pricing API 1220, the pharmacy customer eligibility API 1222, and the drug authentication API 1224. The pharmacy API cache database 1226 may supply data to a pharmacy data store 1212 via an outbound ETL scheduled service 1216, and the pharmacy authentication aggregator API 1218 may receive data from the pharmacy data store 1212. An optional drug catalog 1214 may supply data to the pharmacy data store 1212.

As shown in FIG. 12, users may interact with the pharmacy system infrastructure 1202 via a variety of modules. For example, a pharmacy production support module 1206 may communicate with the pharmacy system infrastructure 1202 to allow an administrator to perform various tasks related to the request processing of the pharmacy system infrastructure 1202. A pharmacy service center 1204 communicates between the pharmacy production support module 1206, the pharmacy authentication aggregator API 1218, and the pharmacy data store 1212. A test automation component 1210 may be used to run automated testing of the request processing performed by the pharmacy system infrastructure 1202.

In various implementations, the system 1200 may be used as, for example, a national pre-certification program for medical oncology treatments (or any other suitable treatments) that is supported by evidence based guidelines. The system 1200 may evaluate drug coverage and communicate authorizations to other claim engines or systems, and complete the determinations in substantially real-time to inhibit any delays that could negatively impact the customer.

The system 1200 may include any suitable technologies to implement functionality provided by the system 1200. For example, the system 1200 may include an Oracle Database 12c (or other suitable cloud-based database), a MongoDB database, Java code and documents (such as JSON objects), RESTful application programming interfaces (APIs) and web services, and so on.

In various implementations, Layer 7 security (or application layer security) may be used for email authentication protocols. JavaScript Object Notation (JSON) and extensible markup language (XML) formats may be used for highly customizable and portable implementations, as opposed to flat files. Such flexibility may allow for making changes on the fly. Redhat Drools may be used to manage business logic in the system 1200, such as handing override error codes and so on. These example technologies are provided for purposes of illustration only, and other implementations may use other suitable technologies.

Figure 13:
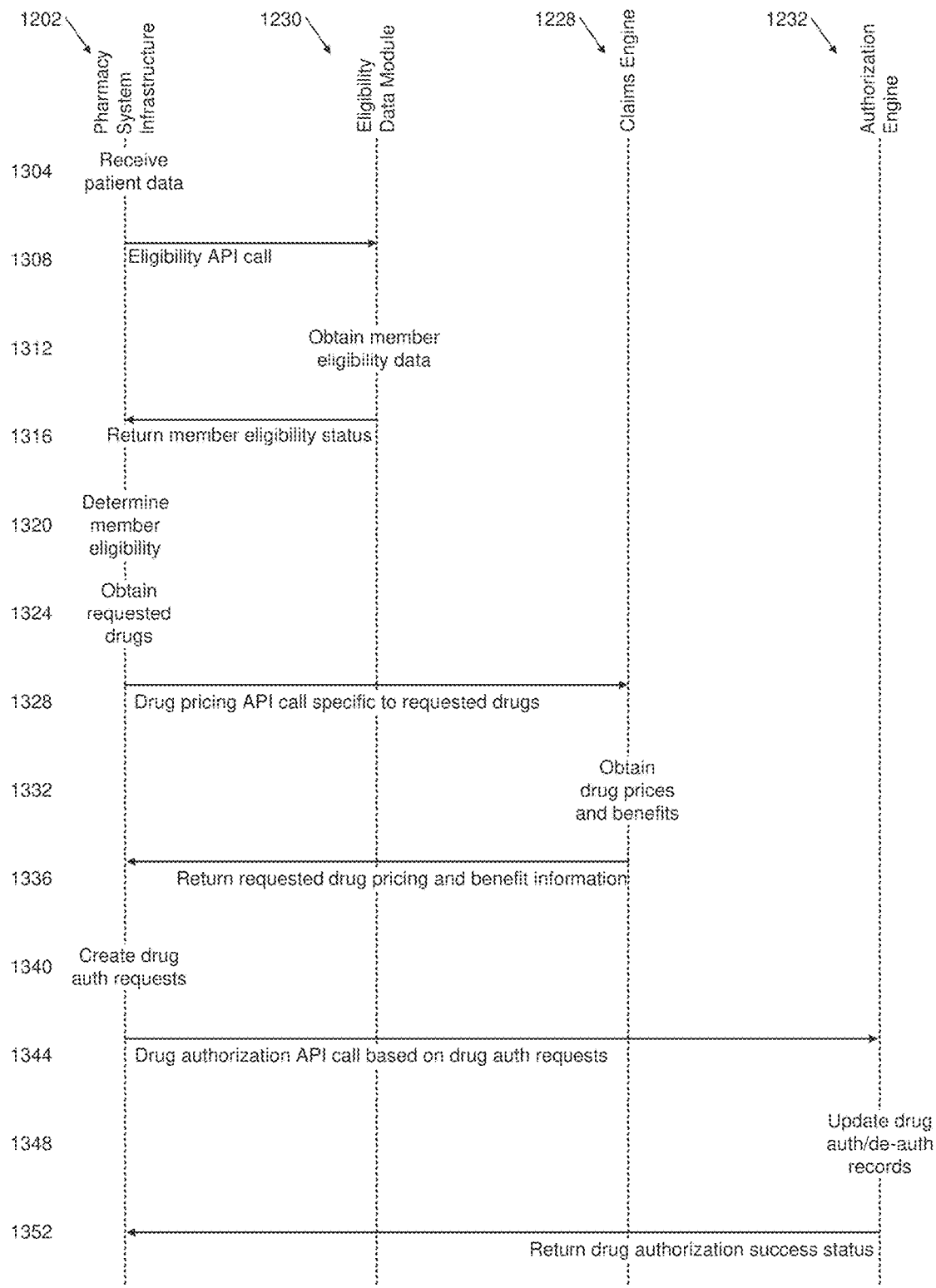
FIG. 13 is a message sequence chart illustrating example interactions between elements of the system of FIG. 12.

FIG. 13 is a message sequence chart illustrating example interactions between the pharmacy system infrastructure 1202, the eligibility data module 1230, the claims engine 1228, and the authorization engine 1232. As shown in FIG. 13, the pharmacy system infrastructure 1202 receives patient data, at line 1304. The pharmacy system infrastructure 1202 then makes an eligibility API call to the eligibility data module 1230, at line 1308.

In response to the eligibility API call, at line 1312, the eligibility data module 1230 obtains member eligibility data. The eligibility data module 1230 returns a member eligibility status to the pharmacy system infrastructure 1202, at line 1316. For example, the pharmacy system infrastructure 1202 may receive data from a provider in order to identify a specific patient, and use an API call to the eligibility data module 1230 to determine whether the identified patient is eligible for drug coverage.

At line 1320, the pharmacy system infrastructure 1202 determines member eligibility. For example, the pharmacy system infrastructure 1202 may determine member eligibility based on the member eligibility status returned via the eligibility API call to the eligibility data module 1230. The pharmacy system infrastructure 1202 then obtains requested drugs at 1324. For example, the requested drugs may be part of a drug regimen selected by a provider.

At line 1328, the pharmacy system infrastructure 1202 makes a drug pricing API call specific to the requested drugs, to the claims engine 1228. The claims engine 1228 then obtains drug prices and benefits at line 1332. The claims engine 1228 returns requested drug pricing and benefit information to the pharmacy system infrastructure 1202 at line 1336. For example, after the pharmacy system infrastructure 1202 obtains the requested drugs, it may use an API call to the claims engine 1228 to obtain prices and related benefit information for the drugs that are specific to the selected regimen.

At 1340, the pharmacy system infrastructure 1202 creates drug authorization requests, which may include the drug pricing and benefit information returned via the API call to the claims engine 1228. At line 1344, the pharmacy system infrastructure 1202 makes one or more drug authorization API calls based on the generated drug authorization requests, to the authorization engine 1232. The authorization engine 1232 updates the drug authorization and de-authorization records at line 1348, and returns one or more drug authorization success statuses to the pharmacy system infrastructure 1202 at line 1352.

Automated Drug Authorization Process

Figure 14:
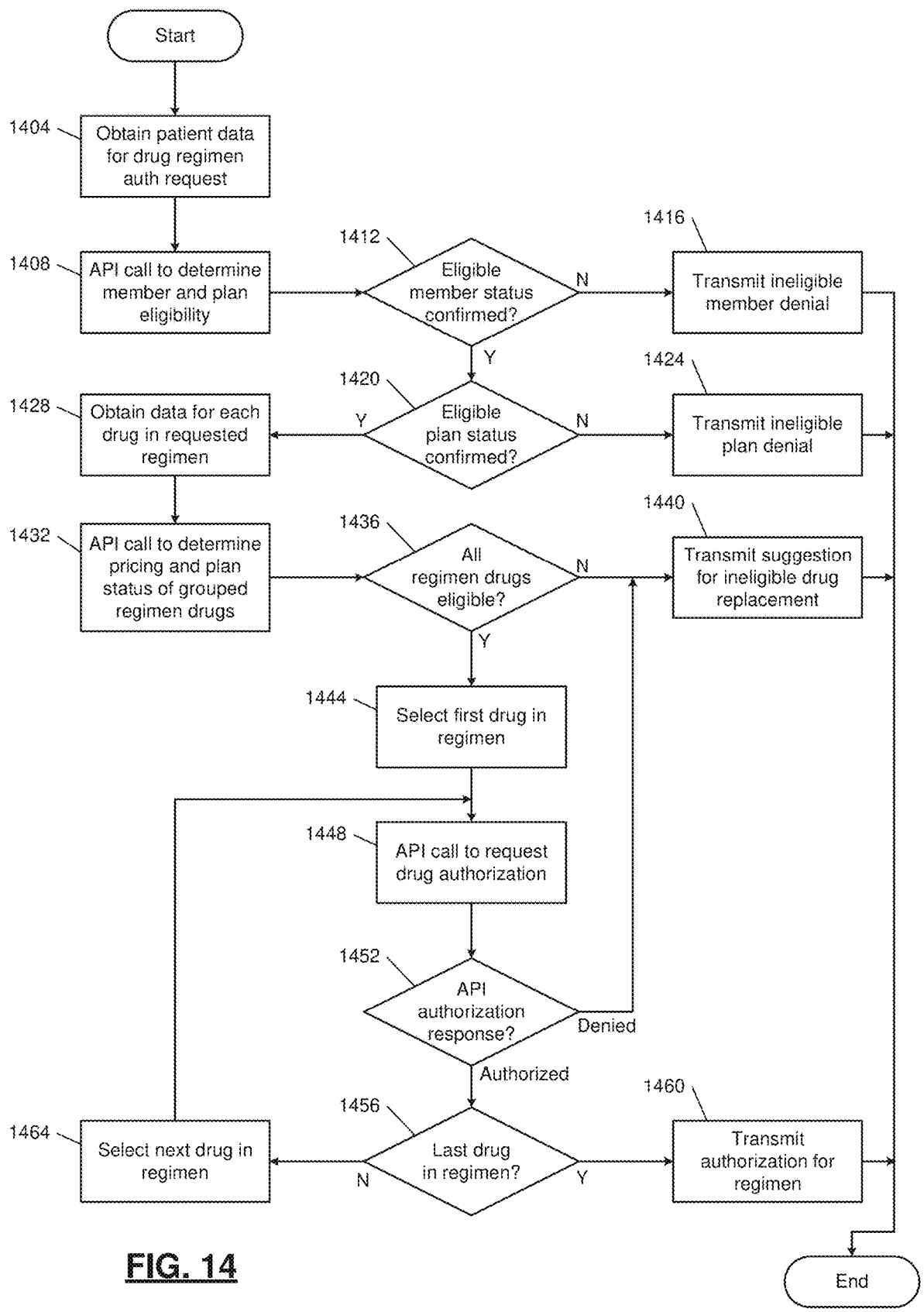
FIG. 14 is a flowchart illustrating an example method of using API call to obtain authorizations for a drug regimen.

FIG. 14 is a flowchart illustrating an example method of using one or more API calls to obtain authorizations for a drug regimen. At 1404, control begins by obtaining patient data for a drug regimen authorization request. Control then makes an API call at 1408 to determine member and plan eligibility, such as an API call to the eligibility data module 1230 of FIG. 12.

If control determines at 1412 that a member eligibility status has not been confirmed, control proceeds to 1416 to transmit a member eligibility denial, such as transmitting the denial to a provider via the pharmacy service center 1204 of FIG. 12. If control determines at 1412 that a member eligibility status has been confirmed, control determines proceeds to 1420 to determine whether an eligible plan status has been confirmed. If not, control transmits a plan eligibility denial at 1424. For example, control may use the API call to determine whether a member is eligible for drug coverage, and whether the member's health plan allows for drug coverage. If not, control may transmit appropriate denial indications based on member ineligibility or plan eligibility.

After eligibility plan status is confirmed at 1420, control proceeds to 1428 to obtain data for each drug in the requested regimen. For example, a provider may select a drug regimen that includes multiple drugs, and control may obtain data related to each drug in the regimen selected by the provider by making an API call to determine pricing and plan status of the group of regimen drugs at 1432.

At 1436, control determines whether all regimen drugs are eligible. If not, control transmits a suggestion for an eligible drug replacement at 1440. For example, control may screen each drug in the regimen to make an initial determination if any of the drugs are known to be ineligible for authorization, prior to making drug authorization requests for each drug individually. If a drug is known to be ineligible (for example, based on the member's health plan coverage), control may suggest a similar drug that may be eligible for coverage to replace the ineligible drug in the regimen.

If control determines at 1436 that all regimen drugs are eligible, control proceeds to 1444 to select the first drug in the regimen. Control then makes an API call to the request authorization for the first drug at 1448. At 1452, control analyzes the API authorization response. If the API authorization response is a denial, control proceeds to 1440 to transmit a suggestion for an eligible drug replacement (for example, a suggestion of a similar drug that may be authorized under the member's health plan).

When the API authorization response is a successful authorization at 1452, control proceeds to 1456 to determine whether the last drug in the regimen has been processed. If not, control selects the next drug in the regimen at 1464, and returns to 1448 to make an API call to request drug authorization for the next selected drug. When control determines at 1456 that the last drug in the regimen has been selected, control proceeds to 1460 to transmit one or more authorizations for the regimen.

In various implementations, the system may evaluate information gathered during clinical review and determine which drugs likely belong under the pharmacy benefit. The system may create a data packet and send a real-time ping (such as a claims test) to a claim processing system to confirm member eligibility and whether the drug is covered under a pharmacy benefit. APIs may interface with a claim engine and send a real-time response back for confirmation and/or to provide a message to a prescriber. "Real-time" may refer to an action that takes place in a very short period of time relative to a user's perception, such as less than 10 milliseconds, less than 100 milliseconds, less than one second, less than one minute, as so on, as opposed to a process that requires, for example, several hours, overnight processing, or longer.

Once approved, the pharmacy drug authorizations may be repackaged and transmitted in real-time back to a claims engine, where the repackaged drug authorizations are loaded and made available for claims payment. The system may include IT integration that provides member eligibility checking, member drug price information, and member drug authorization via RESTful APIs. The RESTful APIs may be used by internal/external vendors to perform multiple operations in support of real-time transactions for prior authorizations.

For example, regarding member/family eligibility, a standalone operation within a pharmacy API may support a request for customer information based on eligibility from a pharmacy management system or a home delivery pharmacy store. In various implementations, the API call may be performed with a response time on the order of milliseconds, to first check whether a member is eligible for potential drug authorization (such as whether the member is part of a covered health plan and has pharmacy benefits).

Regarding drug pricing, a standalone operation within the Pharmacy API may support a request to price a drug against a pharmacy management benefit plan for a customer. This will inform the requester whether the drug is covered under the customer's benefit plan, as well as the liability amounts. The drug pricing service may receive one or more data inputs, such as treatment case information (like an episode/case identifier), patient demographics, and drug information, to validate whether the drug is covered under a pharmacy benefit of the customer's health plan.

This may be executed via a process referred to as a claims test. In various implementations, the claims test may be used for each drug of a drug regimen provided by, for example, a medical oncology service. The drug pricing service may be used for suggesting other drugs if a certain drug is denied, and may obtain information needed for each drug for submission in a subsequent API for authorization.

For example, a first API may be used to obtain drug pricing information for all drugs within a regimen via a single API call, where multiple subsequent API calls are made separately for each drug to obtain individual authorizations for each drug in the regimen. In this manner, a single request can be made by a provider for a full drug regimen, where the system automates prior authorization checks and authorization requests for each drug in the regimen on its own, possibly without further intervention by the provider. If obtained drug benefit data indicates that a drug is not covered under a patient's benefit coverage, the system may replace the drug with another related drug that is covered for the patient. For example, the system may search for another drug that has a related national drug code (NDC).

In various implementations, drug authorization creation and disabling may be performed by a drug authorization service that receives data inputs such as treatment case information (like an episode/case identifier), an operation type, patient identifiers, and the requested drug, to attempt to load or deactivate authorization records under the a pharmacy benefit of the customer's health plan. A claim service may provide a standalone operation within a pharmacy API that supports a request to get pharmacy claim data from a pharmacy database, such as Amazon Web Services RDS, MongoDB DAL, and so on. For example, a claims service API call may be executed to a pharmacy claim database, to store a log of structured compliance data associated with drug authorization approvals or denials.

Example API request mappings for attribute names and API fields are listed in Table 1 below. Example API response mappings of field names and API mapping fields are listed in Table 2 below.

TABLE 1

| Attribute name | API Field |
| --- | --- |
| Request System | Header (Request-System) |
| Request Type | Resource Parameter |
| | GC-members/eligibility |
| | PD-members/drugs/pricing |
| | CA-members/drugs/authorization/create |
| | DA-members/drugs/authorization/disable |
| External Transaction Number | externalTransactionId |
| Eligibility Date | eligibilityDate |
| Eligibility System | typeCode |
| Account Number | accountId |
| Benefit Option | benefitPlanCode |
| Member Identifier | identifier.IdTypeCode("MID"), Identifier.id |
| Member Alternate Identifier | Identifier.IdTypeCode("AMI"), Identifier.id |
| First Name | firstName |
| Middle Name | middleInitial |
| Last Name | lastName |
| Date of Birth | dateOfBirth |
| Gender | genderCode |
| Eligibility Type | eligibilityTypeCode |
| Prescriber ID | drug.prescriberId |
| Prescriber ID Type | drug.prescriberIdTypeCode |
| Pharmacy Identifier | drug.pharmacyId |
| Pharmacy Identifier type | drug.pharmacyIdTypeCode |
| GCN | drug.id, drug.idTypeCode("GCN") |
| Day Supply Count | drug.supplyDayCount |
| Metric Unit Quantity | drug.metricUnitQuantity |
| Drug name | drug.name |
| Authorization Type | drug.authorization.typeCode |
| Authorization number | drug.authorization.id |
| Authorization Effective Date | drug.authorization.effectiveDate |
| Authorization Expiration Date | drug.authorization.expirationDate |
| refillCount | Drug.authorization.refillCount |
| Reject Category code | drug.authorization.rejectCategoryCode |

TABLE 2

| Field name | API Mapping field |
| --- | --- |
| Request Date | Not Required (EviCore can use Requested TimeStamp) |
| Request Identifier | serviceReferenceId |
| Response Date | Not Required (EviCore can use received TimeStamp) |
| Response System | Not required as it is differentiated by API URI |
| External Transaction Number | externalTransactionId |

TABLE 2-continued

| Field name | API Mapping field |
| --- | --- |
| Response Category | Not Required as resource is differentiating response |
| Response Type | MetaData.outcome.additionalDetais[ ].code |
| Response Type Description | MetaData.outcome.additionalDetais[ ].message |
| Eligibility Indicator | member.eligibility.eligibilityStatus |
| Eligibility System | typeCode |
| Account Number | accountId |
| Benefit Option | benefitPlanCode |
| Member Identifier | Identifier.IdTypeCode("MID"), identifier.Id |
| Member Alternate Identifier | Identifier.IdTypeCode("AMI"), identifier.Id |
| First Name | firstName |
| Last Name | lastName |
| Date of Birth | dateOfBirth |
| Item Level Response Type | Message.Code(It may be members/drugs) |
| Item Level Response Type Description | Message.detail(It may be members/drugs) |
| Drug name | member.drug.name |
| Reject Type | member.drug.errorCodes.Code |
| Reject Type Descr | member.drug.errorCodes.detail |
| Ignore Indicator | member.drug.errorCodes.ignoreCode |
| Deny Indicator | member.drug.errorCodes.denyIndicator |
| Authorization Number | member.drug.authorization.id |
| Reject Category Code | member.drug.authorization.errorCategoryCode |
| Label Name | member.drug.labelName |
| Brand Generic Indicator CD/NM | member.drug.drugTypeCode |
| Member Liability Amount | member.drug.memberLiabilityAmount |
| Plan Liability Amount | member.drug.planLiabilityAmount |
| Standard Copay Amount | member.drug.standardCopayAmount |
| Standard Coinsurance Amount | member.drug.standardCoinsuranceAmount |
| Standard Deductible Amount | member.drug.deuctibleAmount |
| GCN | drug.id, drug.idTypeCode("GCN") |

In various implementations, the system may establish pre-certification review to ensure that evidence-based treatment regimens are implemented (for example, as defined by the national comprehensive cancer network (NCCN) pathways) to provide cancer treatment. The system may collect clinical information and integrate the information with other claims data to develop future reimbursement bundles, in order to meet the needs of specialty care collaboration teams. The system may provide one or more advantages, such as real-time processing of claim test transactions using Restful APIs, reducing practice variance and improving cost savings and quality, identifying under and over utilization of cancer support therapies, redirecting to clinically optimal therapies and sites of care, improving the accuracy of claims adjudication, guiding physicians to the optimal treatment plan based on the patient's condition, and ensuring proactive identification and care coordination with oncology case management programs/clinical operations.

Figure 15:
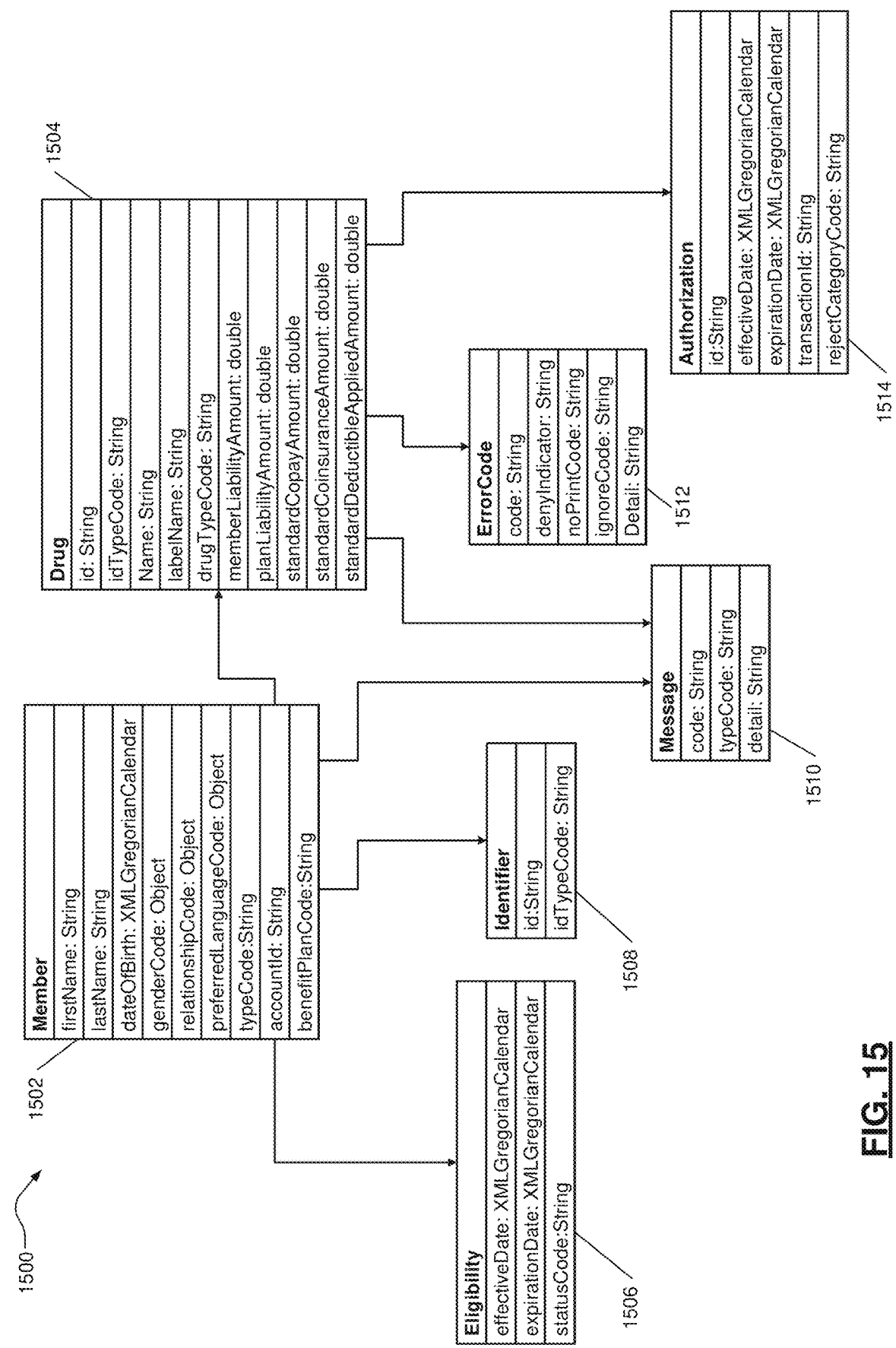
FIG. 15 is an example data model of drug regimen data that may be stored by the system of FIG. 12.

FIG. 15 is an example data model of drug regimen data that may be stored by the system of FIG. 12. The data model 1500 includes an example Member data element 1502 that is linked with other data elements including a Drug data element 1504, an Eligibility data element 1506, an Identifier data element 1508, and a Message data element 1510.

As shown in FIG. 15, the Drug data element 1504 is linked with a Message data element 1510, an ErrorCode data element 1512, and an Authorization data element 1514. The arrangement of data elements in FIG. 15 is for purposes of illustration only, and other implementations may use any other suitable arrangement of data elements.

Automated Database Entry Linking Management System

Figure 16:
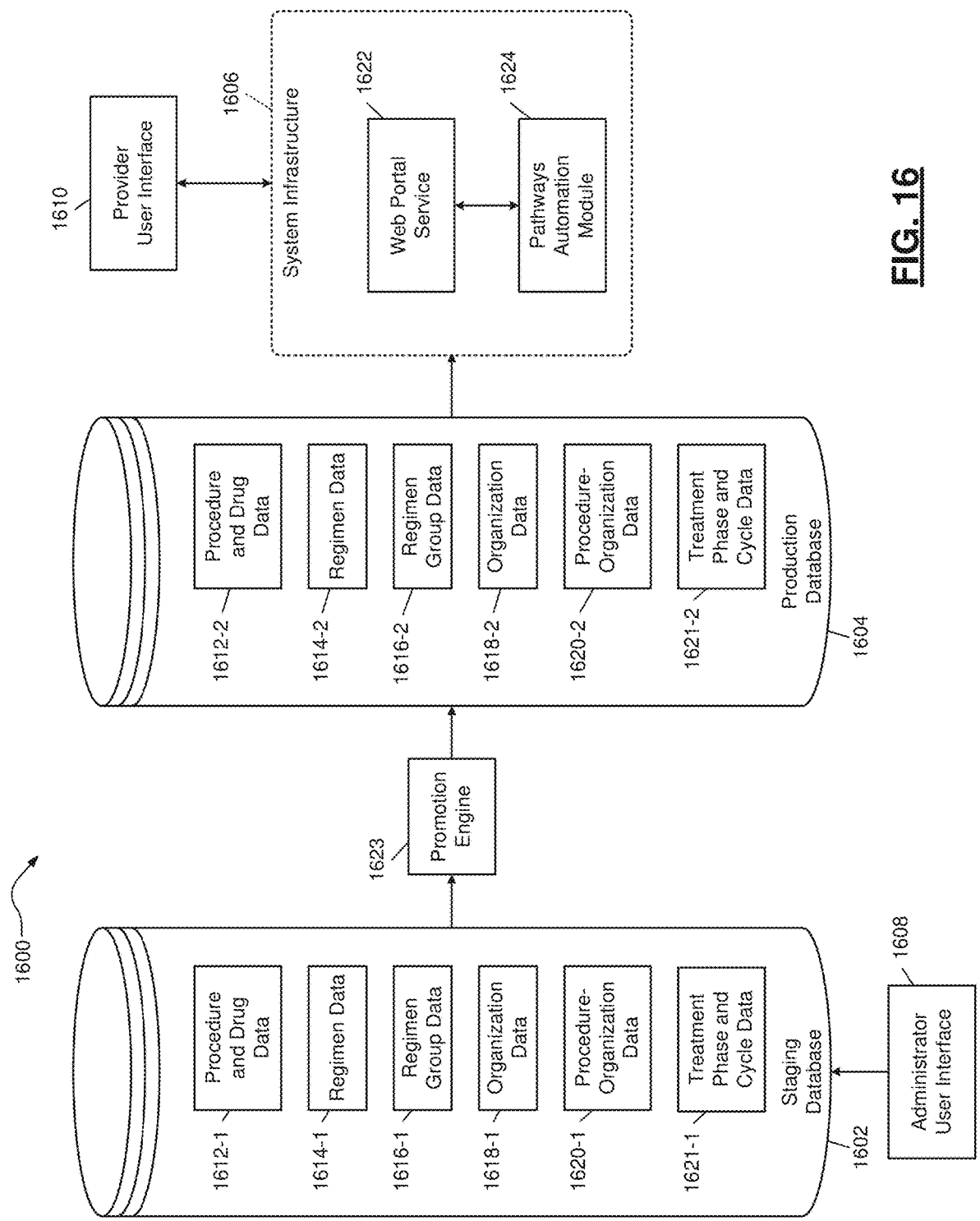
FIG. 16 is a functional block diagram of an example system for automated linking management of regimen database entries.

FIG. 16 is a functional block diagram of an example system 1600 for automated linking management of regimen database entries (sometimes referred to as database entities), which includes a staging database 1602, a production database 1604, and a system infrastructure 1606. While the system 1600 is generally described as being deployed in a computer network system, the staging database 1602, production database 1604, and system infrastructure 1606, and/or other components of the system 1600, may otherwise be deployed (for example, as a standalone computer setup). The system 1600 may include a desktop computer, a laptop computer, a tablet, a smartphone, etc.

As shown in FIG. 16, the staging database 1602 stores procedure and drug data 1612-1, regimen data 1614-1, regimen group data 1616-1, organization data 1618-1, procedure-organization data 1620-1, and treatment and phase cycle data 1621-1. Similarly, the production database 1604 stores procedure and drug data 1612-2, regimen data 1614-2, regimen group data 1616-2, organization data 1618-2, procedure-organization data 1620-2, and treatment and phase cycle data 1621-2. In various implementations, the staging database 1602 and the production database 1604 may store other types of data as well. The data stored in the production database 1604 may include substantially similar copies of data stored in the staging database 1602. For example, the promotion engine 1623 may push data from the staging database 1602 to the production database 1604 on a scheduled basis (such as nightly) and/or at the request of a user.

The procedure and drug data 1612-1, regimen data 1614-1, regimen group data 1616-1, organization data 1618-1, procedure-organization data 1620-1, treatment and phase cycle data 1621-1, procedure and drug data 1612-2, regimen data 1614-2, regimen group data 1616-2, organization data 1618-2, procedure-organization data 1620-2, and treatment and phase cycle data 1621-2, may be located in different physical memories within the staging database 1602 and/or the production database 1604, such as different random access memory (RAM), read-only memory (ROM), a nonvolatile hard disk or flash memory, etc. In some implementations, the procedure and drug data 1612-1, regimen data 1614-1, regimen group data 1616-1, organization data 1618-1, procedure-organization data 1620-1, treatment and phase cycle data 1621-1, procedure and drug data 1612-2, regimen data 1614-2, regimen group data 1616-2, organization data 1618-2, procedure-organization data 1620-2, and treatment and phase cycle data 1621-2 may be located in the same memory (such as in different address ranges of the same memory). In various implementations, the procedure and drug data 1612-1, regimen data 1614-1, regimen group data 1616-1, organization data 1618-1, procedure-organization data 1620-1, treatment and phase cycle data 1621-1, procedure and drug data 1612-2, regimen data 1614-2, regimen group data 1616-2, organization data 1618-2, procedure-organization data 1620-2, and treatment and phase cycle data 1621-2, may each be stored as structured data in any suitable type of data store.

The system infrastructure 1606 may include one or more modules, services, and so on, for performing authorization request processing for drug regimens. For example, FIG. 16 illustrates a web portal service 1622 in communication with a pathways automation module 1624. A provider may access a provider user interface 1610 to communicate with the system infrastructure 1606 to request authorization for a drug regimen. The system infrastructure 1606 may use the web portal service 1622 and pathways automation module 1624 to obtain a selection of a drug regimen from the provider (for example, based on clinical responses submitted by the provider), and obtain corresponding data for obtaining authorization for each drug of the selected regimen from the production database 1604.

As shown in FIG. 16, an administrator user interface 1608 may be used to access the staging database 1602, for example, to update the data stored in the staging database 1602, to change an arrangement of the data stored in the staging database 1602, and so on. The administrator user interface 1608 and the provider user interface 1610 may include any suitable user device for displaying text and receiving input from a user, including a desktop computer, a laptop computer, a tablet, a smartphone, etc. The administrator user interface 1608 and the provider user interface 1610 may access the staging database 1602 and/or system infrastructure 1606 directly, or through one or more networks. Example networks may include a wireless network, a local area network (LAN), the Internet, a cellular network, etc.

In various implementations, the system 1600 may be used as a treatment planner internal facing tool including a web based user interface and one or more underlying databases designed to house and maintain data needed to process prior authorization requests. The system may be used to manage drug data for any suitable medical practice, such as an oncology program, and in various implementations may manage data related to any medical procedure identified by a standard code such as a current procedural technology (CPT) code.

In addition to housing the procedures (such as prescription drugs), the system 1600 may provide other advantages such as managing details specific to a drug (sometimes referred to as drug attributes) like standard units, alternate descriptions, alternate coding conventions like national drug code (NDC) or generic code number (GCN), and so on. The system 1600 may define relationships between drugs by combining them into treatments or regimens, and may customize drug attributes and relationships at the organization (for example, health plan) level to support unique customer requirements for managing and communicating results of a prior authorization request.

In various implementations, the system 1600 may allow business and clinical teams to quickly add and edit procedure/drug data and their relationships into one or more testing environments, and then rapidly push that data into one or more production environments (for example, without IT support). The system 1600 may allow display of multiple, complex treatment options to a requestor through a web portal, as required for a clinical decision support program.

Figure 17:
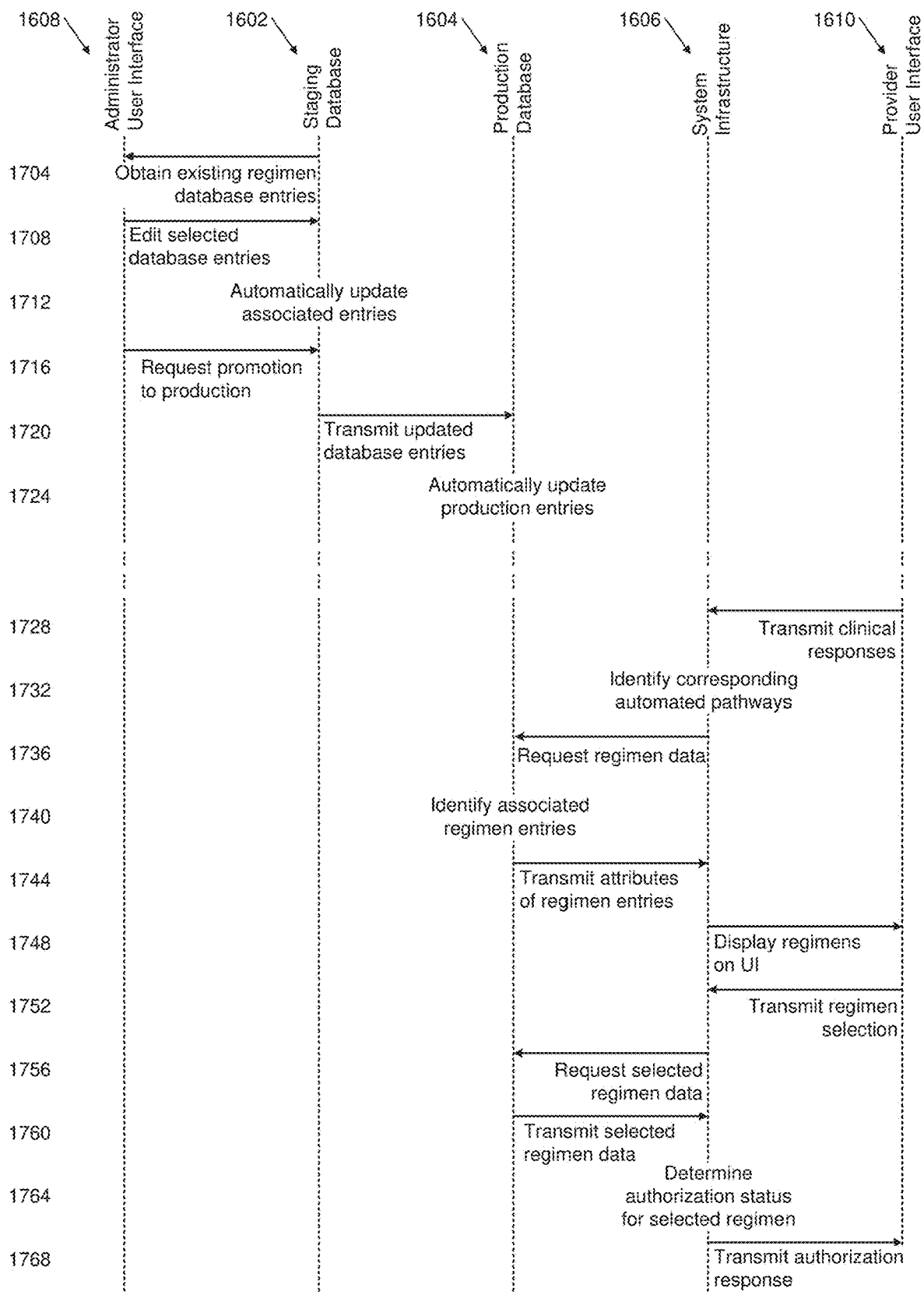
FIG. 17 is a message sequence chart illustrating example interactions between elements of the system of FIG. 16.

FIG. 17 is a message sequence chart illustrating example interactions between elements of the system 1600 of FIG. 16, including the administrator user interface 1608, the staging database 1602, the production database 1604, the system infrastructure 1606, and the provider user interface 1610. At line 1704, the staging database 1602 obtains existing regimen database entries from the administrator user interface 1608.

At line 1708, the administrator user interface 1608 edits selected database entries in this staging database 1602. The staging database 1602 then automatically updates associated entries at line 1712. For example, an administrator may access the staging database 1602 to make changes to database entries when updating drug information for different regimens, for updating data on how different organizations handle different drugs, and so on.

At line 1716, the administrator user interface 1608 requests promotion to production. At line 1720, the staging database 1602 then transmits updated database entries to the production database 1604. For example, the promotion engine 1623 of FIG. 16 may be used to make copies of updated entries in the staging database 1602, for storing in the production database 1604. The production database 1604 then automatically updates the production database entries at line 1724. Although FIG. 17 illustrates the administrator user interface requesting a promotion to production, in various implementations the promotion of data from the staging database 1602 to the production database 1604 may happen on a scheduled basis, such as hourly, nightly, weekly, and so on.

Line 1728 illustrates the beginning of an example process for a provider to request authorization for a drug regimen. At 1728, the provider user interface 1610 transmits clinical responses to the system infrastructure 1606. For example, one or more control pathways may be used to obtain clinical data of a patient's condition from the provider, or to identify appropriate drug treatments for the patient. At line 1732, the system infrastructure 1606 identifies corresponding automated pathways for the clinical responses submitted by the provider.

At line 1736, the system infrastructure 1606 requests regimen data from the production database 1604. The production database 1604 then identifies associated regimen entries at line 1740. The production database 1604 transmits attributes of the regimen entries to the system infrastructure 1606 at line 1744. The system infrastructure 1606 then displays the regimen entries on the UI of the provider user interface 1610, at line 1748.

For example, based on the clinical responses submitted by the provider, the system infrastructure 1606 may use pathways to access the production database 1604 to identify multiple drug regimens that correspond to the clinical responses submitted by the provider. The multiple drug regimens may then be displayed for the provider to make a selection of their desired drug regimen to treat the patient. At line 1752, the provider user interface 1610 transmits a regimen selection to the system infrastructure 1606.

At line 1756, the system infrastructure 1606 requests selected regimen data from the production database 1604. For example, the system infrastructure 1606 may request data for each drug within the regimen selected by the provider. At 1760, the production database 1604 transmits data for the selected regimen back to the system infrastructure 1606. The system infrastructure 1606 then determines authorization status for the selected regimen, such as an authorization for each individual drug within the regimen, at line 1764. The system infrastructure 1606 then transmits an authorization response to the provider user interface 1610, at line 1768.

Figure 18:
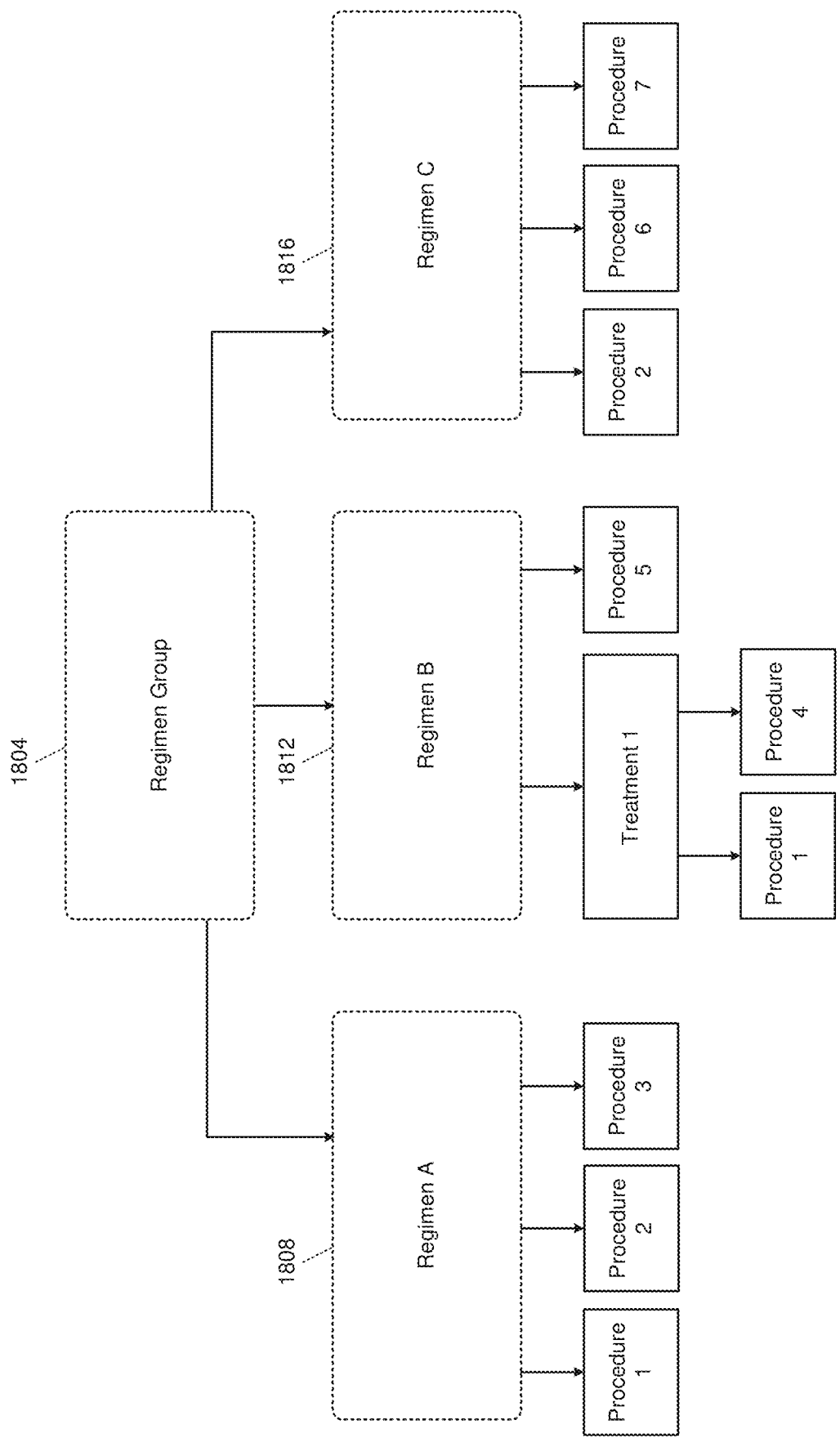
FIG. 18 is a block diagram illustrating example relationships between regimen groups, regimens, treatment groups and procedures.

FIG. 18 is a block diagram illustrating example relationships between regimen groups, regimens, treatment groups and procedures. A regimen group 1804 may include multiple drug regimens that are related to one another in some way, such as different drug regimens that may be used to treat similar patient conditions. As shown in FIG. 18, the regimen group 1804 includes regimen 1808 (Regimen A), regimen 1812 (Regimen B), and regimen 1816 (Regimen C).

The different regimens of the regimen group 1804 may be displayed as different options for a provider to select from, based on clinical responses submitted by the provider. For example, if the provider submits clinical responses that identify the patient as having a specific type of cancer corresponding to the regimen group 1804, the user interface may display each of Regimen A, Regimen B and Regimen C for the provider to select from (for example, for the provider to select which of the three regimens is most suitable to treat the patient).

Each regimen may include one or more treatments groups or procedures, which may overlap with one another. For example, as shown in FIG. 18, the Regimen A includes Procedure 1, Procedure 2, and Procedure 3. Therefore, Regimen A may include three different drugs to be taken by the patient. Regimen B is illustrated as including Procedure 2, Procedure 6 and Procedure 7. In this example, Regimen A and Regimen B each include Procedure 2, while the other procedures/drugs are different between the regimens.

FIG. 18 illustrates Regimen B as including Procedure 5 and Treatment 1, where Treatment 1 includes Procedure 1 and Procedure 4. Treatment groups may be used to group different procedures/drugs for reuse in various Regimens. For example, if Procedure 1 and Procedure 4 are used together often, the group Treatment 1 may be a convenient way for an administrator to more efficiently build additional drug regimens. In various implementations, regimens could have multiple treatment groups, treatment groups may include other treatment groups, treatment groups may include regimens, and so on.

Drug Regimen Authorization Request Process

Figure 19:
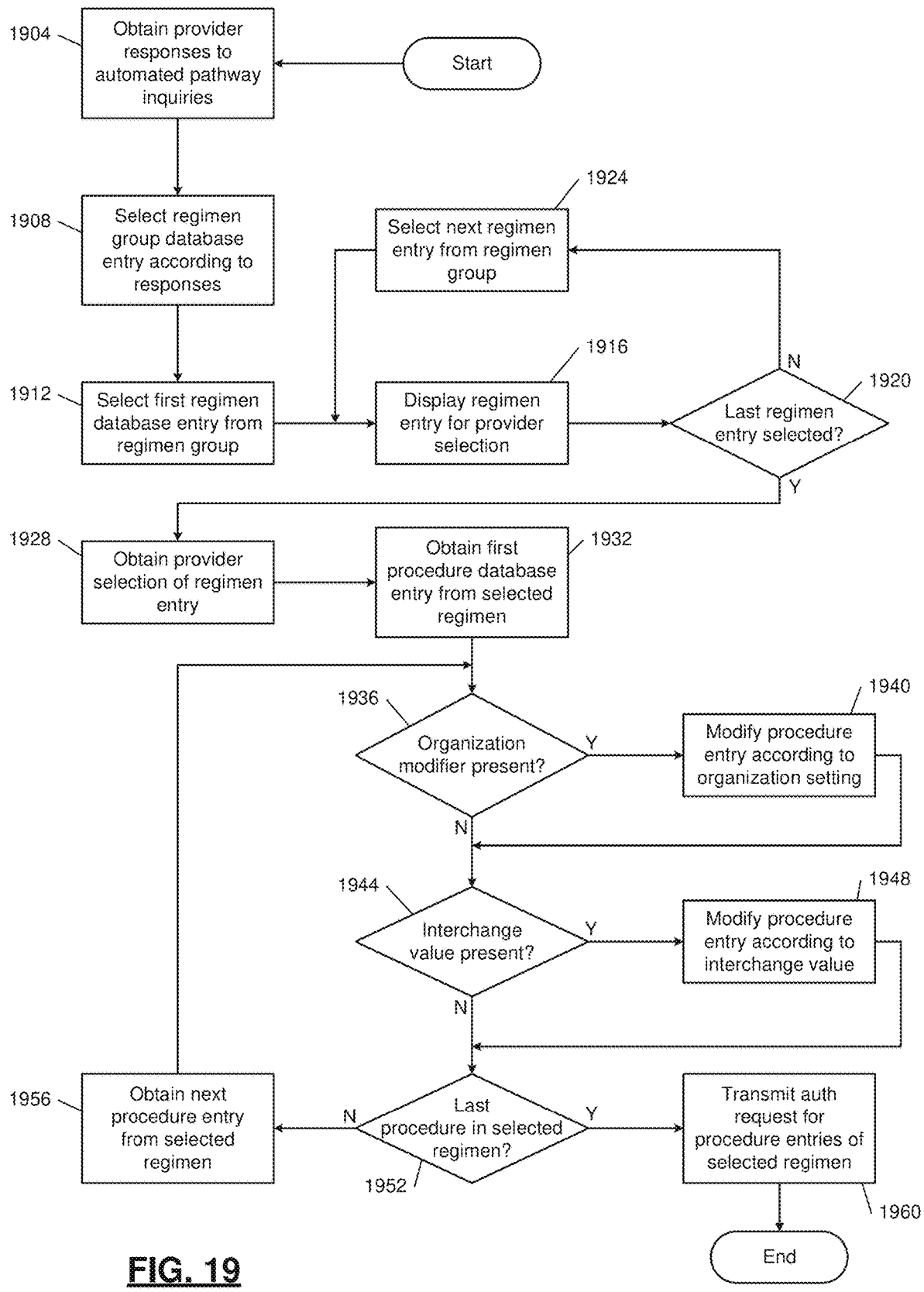
FIG. 19 is a flowchart illustrating an example process of generating an authorization request for multiple drugs of a selected drug regimen.

FIG. 19 is a flowchart illustrating an example process of generating an authorization request for multiple drugs of a selected drug regimen. At 1904, control begins by obtaining provider responses to automated pathway inquiries. For example, a provider may access a user interface to submit clinical responses related to a patient, in order to identify appropriate drug regimen options for treating the patient.

At 1908, control selects a regimen group database entry according to the obtained responses. For example, control may use automated pathways to identify, based on the obtained clinical responses, a group of regimen options that are used to treat patients having conditions identified by the submitted clinical responses. Control then selects a first regimen database entry from the regimen group at 1912.

Control proceeds to 1916 to display the first regimen entry for potential selection by the provider. At 1920, control determines whether the last regimen entry of the regimen group has been selected. If not, control proceeds to 1924 to select the next regimen entry from the regimen group, and then displays the next regimen entry for possible selection by the provider at 1916. For example, control may go through all regimen database entries in the group to display all regimen entries as separate options for selection by the provider.

After all regimen entries from the regimen group have been displayed, control proceeds to 1928 to obtain provider selection of one of the displayed regimen entries. After the provider selects one of the displayed regimen entries, control then obtains the first procedure database entry that belongs to the selected regimen at 1932. For example, when the provider selects one of the displayed regimen entries form the regimen group, control may proceed to obtain information from the database for each procedure/drug belonging to the regimen selected by the provider.

At 1936, control determines whether an organization modifier is present for the procedure database entry. If so, control modifies the procedure entry according to the organization setting at 1940. For example, different organizations may have different requirements for each procedure/drug, and control may modify data about each procedure according to the settings for the organization providing coverage for the current patient.

At 1944, control determines whether interchange values are present for the procedure database entry. If so, control modifies the procedure entry according to an interchange value at 1948. For example, some procedure/drug entries may have interchange values that specify changes to be made to attributes of the drug, specify substitution of another drug, specify drugs or attributes that supersede a currently selected drug, and so on. When an interchange value is present, control may modify the procedure/drug entry within the regimen, such as by substituting another specified procedure/drug according to the interchange value, before transmitting the authorization request for the drug regimen.

At 1952, control determines whether the last procedure in the selected regimen has been processed. If not, control obtains the next procedure entry from the selected regimen at 1956, and returns to 1936 to determine whether an organization modifier is present. Once all drugs within the regimen have been processed, control transmits an authorization request for the procedure entries of the selected regimen at 1960.

FIG. 20 is an illustration of an example GUI for receiving a selection of a drug regimen. For example, the screen 2000 may be displayed to a provider when accessing the system 1600, such as via the provider user interface 1610 of FIG. 16. After submitting clinical information via the provider user interface 1610, the requesting provider may be presented with a list of suggested treatment options (referred to as regimens) as shown in the screen 2000 of FIG. 20.

In various implementations, additional supporting information (referred to as regimen attributes) about those regimens may be provided to assist the provider in selecting a desired regimen. For example, as shown in FIG. 20, the provider is presented with three regimens, or the option to build a custom regimen (which may require additional clinical review outside of an automated prior authorization process). For each regimen, the screen 2000 provides a preferred regimen, a risk of neutropenia, a risk of emesis, a total cost of care during therapy, and a selection frequency. These categories may be configurable by plan and can be changed over time. In various implementations, more or less (or other) parameters may be displayed for each regimen, such as median duration of therapy, a relapse rate within two years, a percentage of all-cause inpatient stays during therapy, and a treatment frequency. The screen 2000 illustrated in FIG. 20 may be a provider facing UI that allows the provider to select a desired regimen, while subsequent example UIs illustrated in FIGS. 21A, 21B, 22A, 22B and 23 may be internal facing UIs that allow an administrator to update the regimen and associated data stored in the system 1600.

FIG. 21A is an illustration of an example GUI for displaying procedure data. As shown in FIG. 21A, the GUI opens to a search screen 2100 that includes five primary tabs designed to manage attributes and relationships of the regimens and drugs. The Procedure tab displays individual medical procedures such as a single drug, and their "universal" attributes (for example, default drug attributes prior to any modification by specific organizations).

The Procedure-Organization tab displays attributes that are specific to different health plans, the Regimen tab displays drug regimens that group combinations of procedures that are commonly used together, and the Regimen Group tab displays combinations of regimens that are related to one another, such as different treatment options for a same clinical condition. The Organization tab displays rules that are specific to different organizations. As shown in FIG. 21A, the Procedure tab may include search capabilities based on, for example, procedure codes or other identifiers, which returns matching procedure(s).

A procedure may be managed by selecting an Edit button. For example, FIG. 21B is an illustration of an example GUI for modifying parameters of a procedure. The Edit screen 2102 allows the user to enter or edit a variety of attributes for a particular procedure/drug. Attributes entered in the Edit screen 2102 may be considered as universal to apply to all organizations.

As shown in FIG. 21B, the Ready for Promotion button may trigger the system to move the new procedure/drug or updated attributes of the procedure/drug into a production environment. Some attributes are entered manually while others, like applicable NDCs, may be loaded and updated based on regular file feeds from external vendors.

Figure 22A:
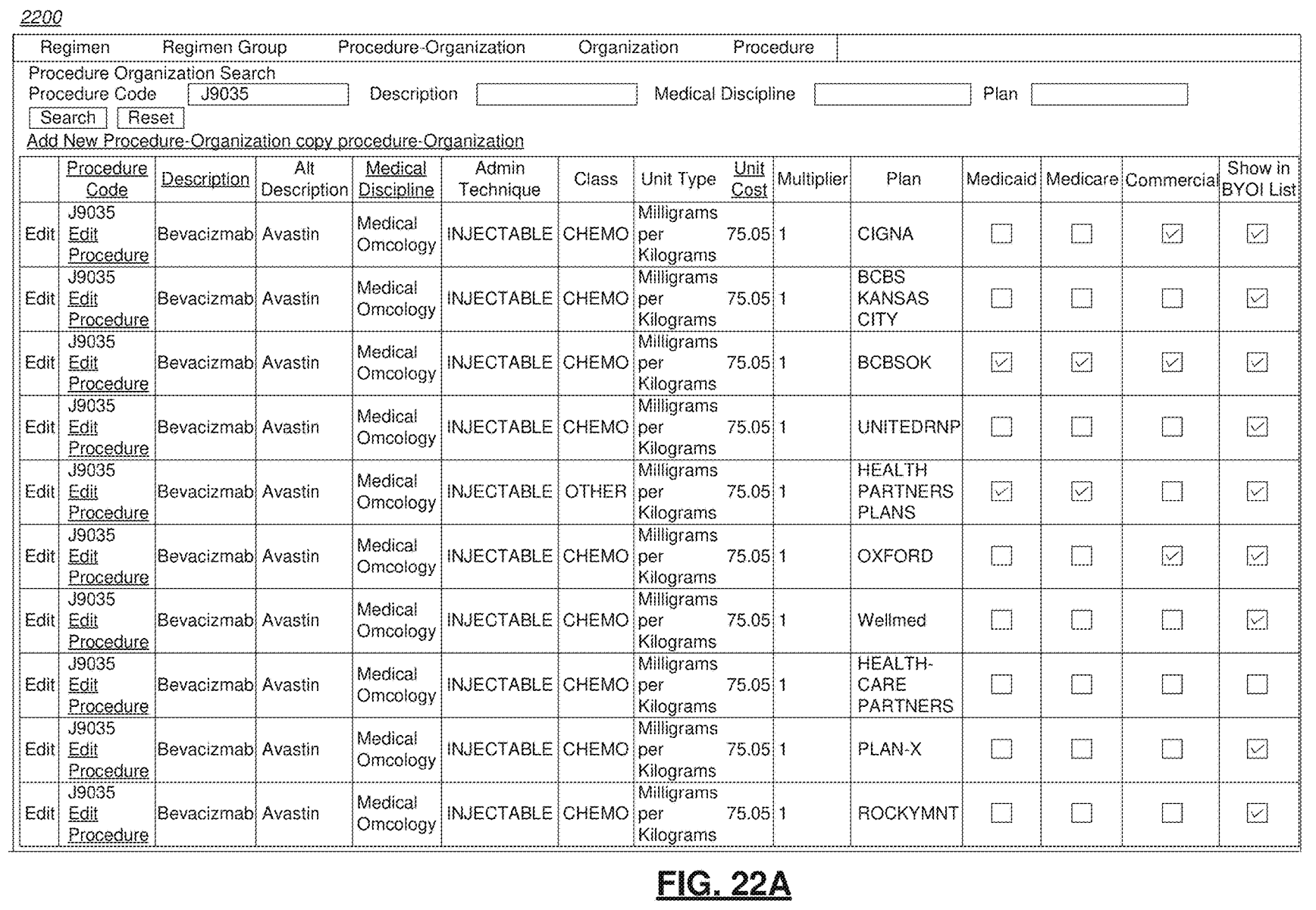

FIG. 22A is an illustration of an example GUI for displaying organization data for multiple procedures. As shown in FIG. 22A, the procedure-organization screen 2200 allows the user to manage how a Procedure is to be handled for each organization individually. For example, different health insurance providers may have different rules for handling prior authorizations for different drugs.

The main view of the screen 2200 may indicates whether a procedure is managed according to specific lines of business (such as Medicaid, Medicare and commercial insurance), along with other organization specific attributes. The Edit button will allow the user to manage other functional attributes specifically for each individual organization.

For example, FIG. 22B is an illustration of an example GUI for modifying parameters of an organization. The screen 2202 may allow a user to set functional rules that apply for all regimens, all regimen groups, and/or all procedures, for a specific organization. As an example, a user may specify a methodology for unit calculation, toggle the dosing functions on and off, and control whether regimen display attributes are shown to a requestor on-screen as well as the order in which the attributes are displayed.

FIG. 23 is an illustration of an example GUI for displaying multiple procedures. As mentioned above, procedures are organized together into groups called regimens, which represent commonly requested treatment plans. Each regimen may be assigned an internal alphanumeric code that indicates, for example, the cancer type the regimen is used to treat, and a sequential number based on when the regimen was created in the system.

As shown in the example screen 2300 of FIG. 23, the associated description for each procedure may be the text that is displayed to the requestor when placing a request through a web portal, or by a nurse when requests are processed by phone. Regimens may be searched by a code, a description, a procedure within a regimen, or by medical discipline.

The Edit button may open a screen with a variety of options for the Regimen. A select button may be used to provide more detailed editing options for regimen attributes. As shown in the screen 2300, all of the procedures in a regimen may be displayed with key attributes such as dosing information. The attributes at this level may be specific to the currently displayed regimen. The Amount for J9035 is 15 in this example, but could be different in another regimen.

Regimen groups may represent a collection of regimens that would typically be used for patients with a certain clinical condition. For example, if clinical evidence suggests that there are four applicable treatment options for a certain clinical condition, those regimens may be placed in a regimen group and displayed to the user side by side when the user is requesting an authorization for a patient with that condition.

Regimen groups may receive a code similar to the regimens, where the first two letters indicate the medical discipline (such as MO for medical oncology), followed by a cancer type abbreviation and then a numeric value.

The regimen group Edit option may allow the user to add and remove regimens from the group, as well as to assign a variety of display attributes to each regimen if desired. These attributes may be set for display on the screen to the requester when the requester is submitting a prior authorization, in order to provide useful information in the decision making process. These values may be unique to the condition for which they are being used, and may be managed at a group level rather than a regimen level. For example, the attributes for a regimen NSCLC41 may different depending on the different groups in which the regimen resides.

Figure 24:
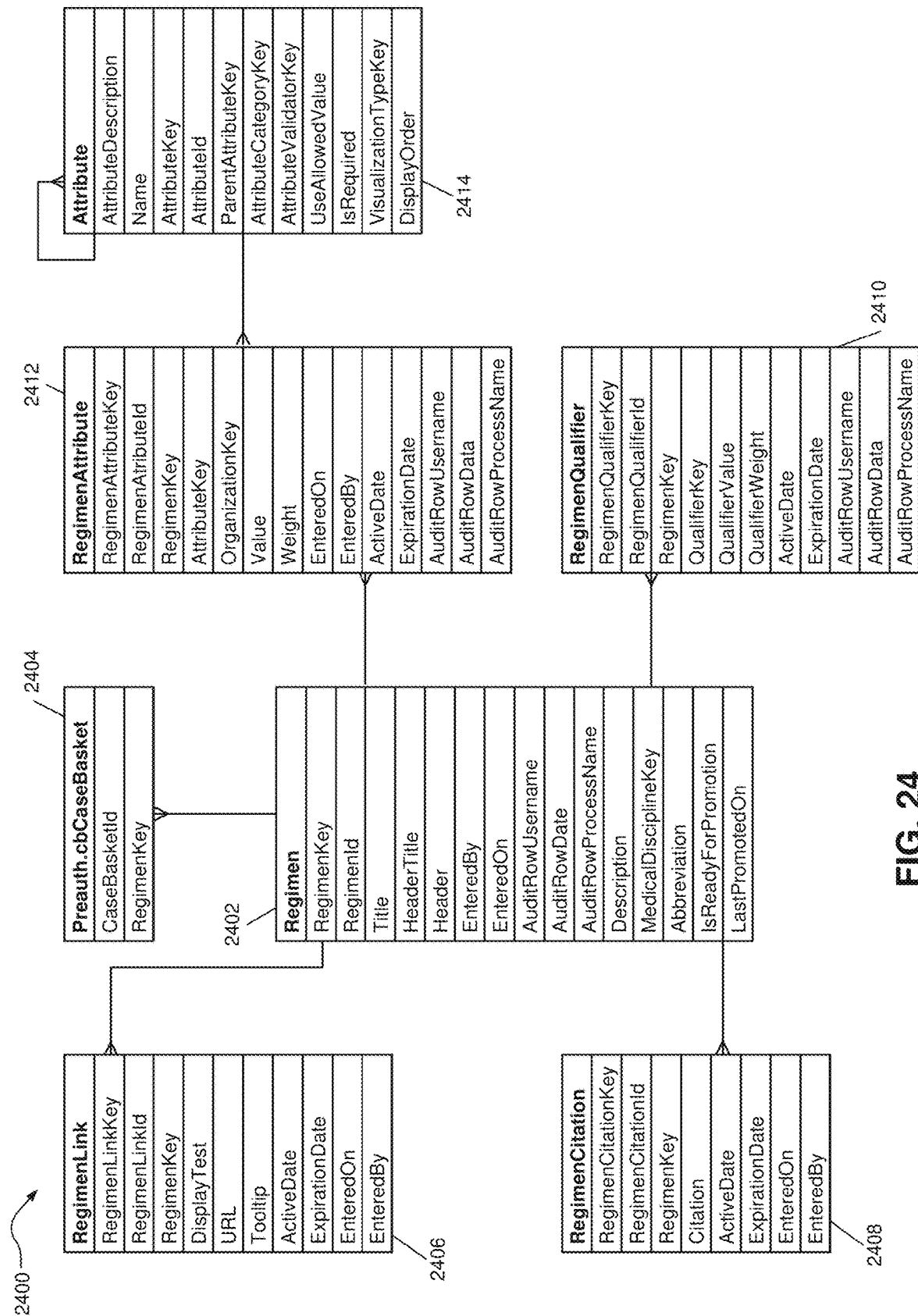
FIG. 24 is an example data model of drug regimen data that may be stored by the system of FIG. 16.

FIG. 24 is an example data model 2400 of drug regimen data that may be stored by the system of FIG. 16. The data model 2400 includes a data element labeled as a Regimen data element 2402, which is linked with other data elements including a Preauth.cbCaseBasket data element 2404, a RegimenLink data element 2406, a RegimenCitation data element 2408, a RegimenQualifier data element 2410, and a RegimenAttribute data element 2412. An Attribute data element 2412 is linked with the RegimenAttribute data element 2412.

Figure 25:
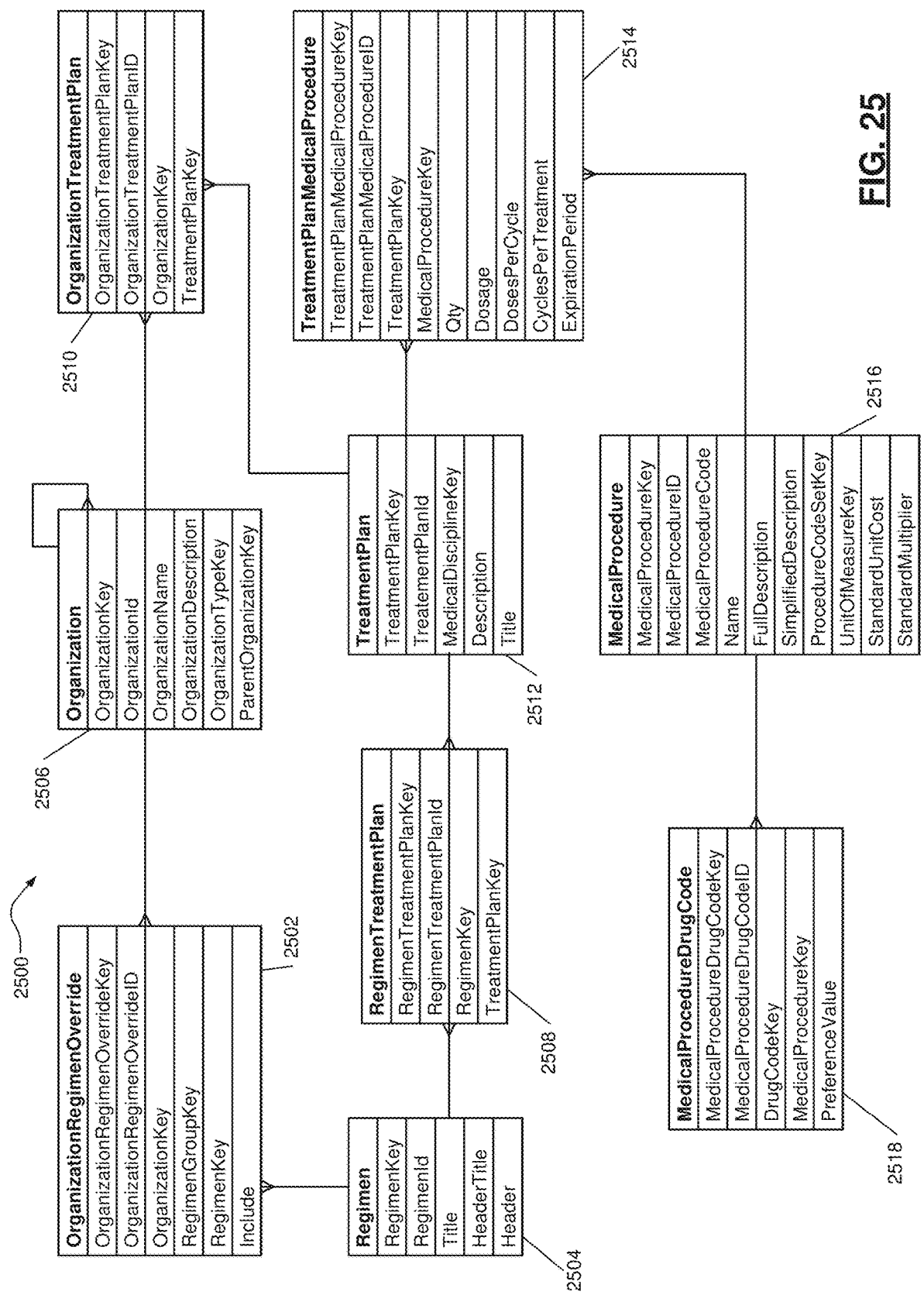
FIG. 25 is an example data model of treatment plan data that may be stored by the system of FIG. 16.

FIG. 25 is an example data model 2500 of treatment plan data that may be stored by the system of FIG. 16. The data model 2500 includes an OrgnizationRegimenOverride data element 2502 that is linked with other data elements including a Regimen data element 2504 and an Organization data element 2506.

A Treatment Plan data element 2512 is linked with a RegimenTreatmentPlan data element 2508, an OrganizationTreatmentPlan data element 2510, and a TreatmentPlanMedicalProcedure data element 2514. The data model 2500 also includes a MedicalProcedure data element 2516 linked with the TreatmentPlanMedicalProcedure data element 2514 and the MedicalProcedureDrugCode data element 2518.

Figure 26:
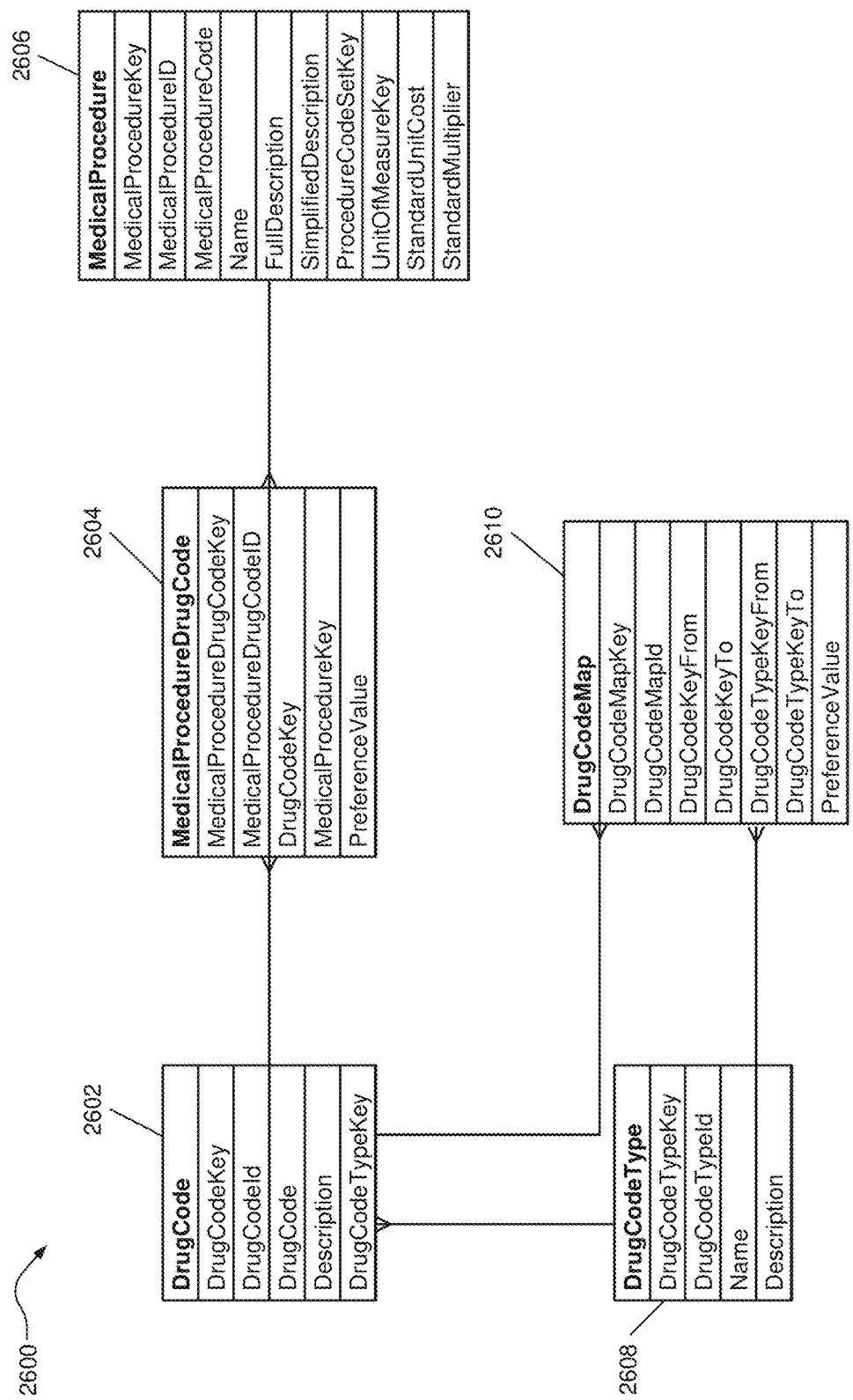
FIG. 26 is an example data model of drug code data that may be stored by the system of FIG. 16.

FIG. 26 is an example data model 2600 of drug code data that may be stored by the system of FIG. 16. The data model 2600 includes a DrugCode data element 2602 that is linked with a MedicalProcedureDrugCode data element 2604 element, a DrugCodeType data element 2608, and a DrugCodeMap data element 2610.

A MedicalProcedure data element 2606 is linked with the MedicalProcedureDrugCode data element 2604. The arrangement of data elements in the data models 2400, 2500 and 2600 are for purposes of illustration only, and other implementations may include other suitable arrangements of data elements.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PUP (PUP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method of generating an automated control pathway for a user interface, the method comprising:

displaying a graphical development environment for generation of the automated control pathway for a prescription drug authorization request, wherein the graphical development environment includes a palette area and multiple graphical programming elements, and wherein the multiple graphical programming elements include at least a question programming element and a determination programming element;

receiving a selection of the question programming element;

displaying the selected question programming element at a location in the palette area specified via user input;

receiving, via user input, at least one answer field specified for the selected question programming element;

displaying at least two pathway branches in the palette area, wherein the at least two pathway branches are associated with the selected question programming element, and the at least one answer field is assigned to one of the at least two pathway branches according to user input;

receiving a selection of the determination programming element;

associating, via user input, the selected determination programming element with the one of the at least two pathway branches;

assigning a status value to the selected determination programming element according to user input, wherein the status value includes a drug request approval indication or a drug request denial indication;

saving the automated control pathway in a production database, wherein the automated control pathway includes the selected question programming element, the selected determination programming element, and the assigned status value for the selected determination programming element;

running the automated control pathway to display a question associated with the selected question programming element on the user interface;
receiving, via the user interface, an answer to the displayed question;
determining the one of the at least two pathway branches associated with the received answer;
automatically transmitting an approval status or a denial status according to the status value assigned to the selected determination programming element associated with the determined one of the at least two pathway branches;
receiving, via the user interface, at least one clinical response indicative of a patient condition;
identifying, via the automated control pathway, at least one drug regimen associated with treatment of the patient condition;
displaying the identified at least one drug regimen via the user interface for selection by a user;
receiving a selection of the at least one drug regimen via the user interface; and
in response to a determination that the selected drug regimen is a national comprehensive cancer network (NCCN) recommended drug regimen, automatically transmitting an approval of an authorization request for the selected drug regimen.

2. The method of claim 1 further comprising, prior to saving the automated control pathway in the production database:
receiving a pathway validation request; and
in response to a determination that the automated control pathway does not include any one of multiple specified major error warnings, saving the automated control pathway to a testing environment, wherein each specified major error warning defines an error in logic of the automated control pathway that prevents operation of the automated control pathway on the user interface.

3. The method of claim 2 further comprising, in response to a determination that the automated control pathway includes at least one specified major error warning:
displaying the at least one specified major error warning;
preventing saving of the automated control pathway to the testing environment at least until a pathway revision is received; and
receiving at least one pathway revision via the graphical development environment.

4. The method of claim 2 further comprising:
in response to a determination that the automated control pathway includes at least one of multiple specified minor error warnings, displaying the at least one of the specified minor error warnings,
wherein each specified minor error warning defines an issue in the logic of the automated control pathway that does not prevent the operation of the automated control pathway on the user interface.

5. The method of claim 2 further comprising:
performing at least one testing operation on the automated control pathway in the testing environment; and
in response to an integration environment request received via user input, deploying the automated control pathway to an integration environment.

6. The method of claim 1 further comprising:
receiving a selection of a plug-in programming element;
displaying the selected plug-in programming element at a location in the palette area specified via user input; and
assigning a call address to the selected plug-in programming element according to user input, wherein the call address specifies an address of a component outside the automated control pathway for the plug-in programming element to retrieve data from.

7. The method of claim 1 further comprising:
receiving a selection of a link programming element;
displaying the selected link programming element at a location in the palette area specified via user input; and
assigning a pathway link to the selected link programming element according to user input, wherein the pathway link specifies a pathway connection between the automated control pathway and another pathway outside of the automated control pathway.

8. The method of claim 1 further comprising:
receiving, via user input, at least one other field specified for the selected question programming element,
wherein the at least one other field includes at least one of a question type field that specifies a type of answer supplied to the question programming element, an answer groups field that lists answer choices a user selects from during operation of the automated control pathway, and a validators field that sets rules for the answer submitted by the user for the question programming element.

9. A computer system comprising:
memory hardware configured to store computer-executable instructions; and
processor hardware configured to execute the instructions, wherein the instructions include:
displaying a graphical development environment for generation of an automated control pathway for a prescription drug authorization request, wherein the graphical development environment includes a palette area and multiple graphical programming elements, and wherein the multiple graphical programming elements include at least a question programming element and a determination programming element;
receiving a selection of the question programming element;
displaying the selected question programming element at a location in the palette area specified via user input;
receiving, via user input, at least one answer field specified for the selected question programming element;
displaying at least two pathway branches in the palette area, wherein the at least two pathway branches are associated with the selected question programming element, and the at least one answer field is assigned to one of the at least two pathway branches according to user input;
receiving a selection of the determination programming element;
associating, via user input, the selected determination programming element with the one of the at least two pathway branches;
assigning a status value to the selected determination programming element according to user input, wherein the status value includes a drug request approval indication or a drug request denial indication;
saving the automated control pathway in a production database, wherein the automated control pathway includes the selected question programming element, the selected determination programming element, and the assigned status value for the selected determination programming element;
running the automated control pathway to display a question associated with the selected question programming element on a user interface;

receiving, via the user interface, an answer to the displayed question;

determining the one of the at least two pathway branches associated with the received answer;

automatically transmitting an approval status or a denial status according to the status value assigned to the selected determination programming element associated with the determined one of the at least two pathway branches;

receiving, via the user interface, at least one clinical response indicative of a patient condition;

identifying, via the automated control pathway, at least one drug regimen associated with treatment of the patient condition;

displaying the identified at least one drug regimen via the user interface for selection by a user;

receiving a selection of the at least one drug regimen via the user interface; and in response to a determination that the selected drug regimen is a national comprehensive cancer network (NCCN) recommended drug regimen, automatically transmitting an approval of an authorization request for the selected drug regimen.

10. The computer system of claim 9 further comprising, prior to saving the automated control pathway in the production database:

receiving a pathway validation request; and in response to a determination that the automated control pathway does not include any one of multiple specified major error warnings, saving the automated control pathway to a testing environment, wherein each specified major error warning defines an error in logic of the automated control pathway that prevents operation of the automated control pathway on the user interface.

11. The computer system of claim 10 wherein the instructions further include, in response to a determination that the automated control pathway includes at least one specified major error warning:

displaying the at least one specified major error warning;

preventing saving of the automated control pathway to the testing environment at least until a pathway revision is received; and receiving at least one pathway revision via the graphical development environment.

12. The computer system of claim 10 wherein the instructions further include:

in response to a determination that the automated control pathway includes at least one of multiple specified minor error warnings, displaying the at least one of the specified minor error warnings, wherein each specified minor error warning defines an issue in the logic of the automated control pathway that does not prevent the operation of the automated control pathway on the user interface.

13. The computer system of claim 10 wherein the instructions further include:

performing at least one testing operation on the automated control pathway in the testing environment; and in response to an integration environment request received via user input, deploying the automated control pathway to an integration environment.

14. The computer system of claim 9 wherein the instructions further include:

receiving a selection of a plug-in programming element;

displaying the selected plug-in programming element at a location in the palette area specified via user input; and assigning a call address to the selected plug-in programming element according to user input, wherein the call address specifies an address of a component outside the automated control pathway for the plug-in programming element to retrieve data from.

15. The computer system of claim 9 wherein the instructions further include:

receiving a selection of a link programming element;

displaying the selected link programming element at a location in the palette area specified via user input; and assigning a pathway link to the selected link programming element according to user input, wherein the pathway link specifies a pathway connection between the automated control pathway and another pathway outside of the automated control pathway.

16. The computer system of claim 9 wherein the instructions further include:

receiving, via user input, at least one other field specified for the selected question programming element, wherein the at least one other field includes at least one of a question type field that specifies a type of answer supplied to the question programming element, an answer groups field that lists answer choices a user selects from during operation of the automated control pathway, and a validators field that sets rules for the answer submitted by the user for the question programming element.

* * * * *